(12) United States Patent
Levy et al.

(10) Patent No.: US 7,560,704 B2
(45) Date of Patent: Jul. 14, 2009

(54) METHOD, DEVICE AND SYSTEM OF ILLUMINATION-BASED DISINFECTION

(75) Inventors: Uri Levy, Rehovot (IL); Zamir Tribelsky, Mevaseret Tzion (IL); Yitzhak Rozenberg, Ramat Gan (IL)

(73) Assignee: Atlantium Technologies Ltd., Beit-Shemesh (IL)

(*) Notice: Subject to any disclaimer, the term of this patent is extended or adjusted under 35 U.S.C. 154(b) by 459 days.

(21) Appl. No.: 11/516,043

(22) Filed: Sep. 6, 2006
(Under 37 CFR 1.47)

(65) Prior Publication Data
US 2007/0119922 A1 May 31, 2007

Related U.S. Application Data

(60) Provisional application No. 60/713,713, filed on Sep. 6, 2005.

(51) Int. Cl.
*G01N 21/00* (2006.01)
(52) U.S. Cl. ........................ 250/438; 250/435
(58) Field of Classification Search .......... 250/438, 250/435, 432 R, 428, 455.11
See application file for complete search history.

(56) References Cited

U.S. PATENT DOCUMENTS

| | | | |
|---|---|---|---|
| 5,124,131 A | 6/1992 | Wekhof | |
| 6,752,971 B2 | 6/2004 | Boehme | |
| 6,940,075 B2 * | 9/2005 | Schulz | 250/432 R |
| 2005/0092932 A1 | 5/2005 | Bircher et al. | |
| 2005/0173351 A1 | 8/2005 | Neofotistos | |

FOREIGN PATENT DOCUMENTS

| EP | 0 893 411 | 1/1999 |
|---|---|---|
| WO | WO 2005/011753 | 2/2005 |

OTHER PUBLICATIONS

International Search Report from International Application No. PCT/IL06/01031 Date of mailing Sep. 13, 2007.
Supplementary European Search Report for App. No. EP 06 78 0463 Date of completion of search Oct. 15, 2008.

* cited by examiner

*Primary Examiner*—Kiet T Nguyen
(74) *Attorney, Agent, or Firm*—Pearl Cohen Zedek Latzer LLP

(57) ABSTRACT

Some demonstrative embodiments of the invention include a method, device and/or system illumination-based disinfection. A disinfector may include, for example, a conduit to carry a flowing medium to be disinfected, the conduit having an inlet to receive the medium and an outlet to discharge the medium; a flow adapter configured to adapt a flow of the medium at the inlet based on an intended spatial distribution of flow velocities of entities suspended in the medium along a plurality of intended flow paths from the inlet to the outlet; and at least one illumination source to illuminate the conduit with light having a customized spatial light flux distribution, which is based at least in part on the intended distribution of flow velocities. Other embodiments are described and claimed.

40 Claims, 18 Drawing Sheets

METHOD, DEVICE AND SYSTEM OF ILLUMINATION-BASED DISINFECTION

CROSS REFERENCE TO RELATED APPLICATIONS

This application claims priority of U.S. Provisional Application No. 60/713,713, filed Sep. 6, 2005, the entire disclosure of which is incorporated herein by reference.

BACKGROUND OF THE INVENTION

Disinfection systems, such as an ultraviolet liquid disinfection system using light radiation, have been long known.

In the disinfection systems the irradiation of the liquid, such as water, with UV light may be used to inactivate microorganisms in the liquid, if the irradiation intensity and exposure duration are above a minimum dose level (often measured in units of miliJoules per square centimeter).

Ideally, UV-based disinfection systems should be constructed such that each microorganism crossing the system is irradiated with the same UV dose. The existing disinfection systems do not have the capability of effectively achieving the delivery of a similar UV dose to microorganisms crossing the system.

SUMMARY OF SOME DEMONSTRATIVE EMBODIMENTS OF THE INVENTION

Some demonstrative embodiments of the invention include a device, system and/or method of illuminating a medium having entities suspended therein.

According to some demonstrative embodiments of the invention, the device may include a conduit to carry a flowing medium to be disinfected. The conduit may have an inlet to receive the medium and an outlet to discharge the medium. The device may also include a flow adapter configured to adapt a flow of the medium at the inlet based on an intended spatial distribution of flow velocities of entities suspended in the medium along a plurality of intended flow paths from the inlet to the outlet. The device may also include at least one illumination source to illuminate the conduit with light having a customized spatial light flux distribution, which is based at least in part on the intended distribution of flow velocities.

According to some demonstrative embodiments of the invention, the customized light flux distribution and the intended spatial distribution of flow velocities may result in an intended distribution of a plurality of cumulative illumination doses corresponding to the plurality of flow paths, respectively. A ratio of a difference between an average of the cumulative illumination doses and a minimum of the cumulative illumination doses to the average may be, for example, smaller than 0.7

According to some demonstrative embodiments of the invention, each of the cumulative illumination doses may include a sum of ratios related to a path of the plurality of paths. The sum of ratios may include a sum of ratios between intended light intensities resulting from the customized light flux at a plurality of locations along the path and intended flow velocities at the plurality of locations.

According to some demonstrative embodiments of the invention, the conduit may include an elongated chamber. In one example, the chamber may include a tubular chamber. A first intended light intensity resulting from the customized light flux at a first distance from a rotation-axis of the chamber may be smaller than a second intended light intensity resulting from the customized light flux at a second distance from the rotation-axis, which is smaller than the first distance. In another example, a first intended light intensity resulting from the customized light flux at a first distance from an inner surface of the chamber may be smaller than a second intended light intensity resulting from the customized light flux at a second distance from the inner surface, which is bigger than the first distance.

According to some demonstrative embodiments of the invention, the illumination source may be external to the conduit.

According to some demonstrative embodiments of the invention, the conduit may include an illumination window to allow light from the illumination source to enter the conduit.

According to some demonstrative embodiments of the invention, one or more optical attributes of the window may be based at least in part on the customized light flux distribution.

According to some demonstrative embodiments of the invention, the one or more optical attributes may include a refractive index of the window in a spectrum of the light.

According to some demonstrative embodiments of the invention, the at least one illumination source may include two or more illumination sources.

According to some demonstrative embodiments of the invention, the two or more illumination sources may include a first set of one or more lamps positioned substantially opposite to a second set of one or more lamps.

According to some demonstrative embodiments of the invention, the two or more illumination sources may include a first set of one or more lamps proximal to the inlet, and a second set of one or more lamps proximal to the outlet.

According to some demonstrative embodiments of the invention, the illumination source may include at least one lamp configured to generate light of a predefined distribution; and at least one reflector to reflect at least part of the light generated by the at least one lamp. The light having the customized light flux distribution may include a combination of the light generated by the lamp and light reflected by the reflector.

According to some demonstrative embodiments of the invention, one or more sections of the reflector may be configured based on one or more local light flux distributions of the customized light flux distribution.

According to some demonstrative embodiments of the invention, the reflector may include an elliptic reflector.

According to some demonstrative embodiments of the invention, the reflector may include a spheroid reflector.

According to some demonstrative embodiments of the invention, a shape of the lamp may be based at least in part on the customized light flux distribution. For example, the lamp may include a donut-shaped lam, or a cross-shaped lamp.

According to some demonstrative embodiments of the invention, one or more attributes of the reflector may be based at least in part on one or more dimensions of the conduit. For example, the one or more dimensions of the conduit may include an inner diameter of the conduit.

According to some demonstrative embodiments of the invention, a configuration of the conduit may be based at least in part on the intended distribution of flow velocities. For example, a configuration of at least one of the inlet and outlet may be based at least in part on the intended distribution of flow velocities.

According to some demonstrative embodiments of the invention, the conduit may include a quartz conduit.

According to some demonstrative embodiments of the invention, the light may include ultraviolet light.

According to some demonstrative embodiments of the invention, the medium may include a liquid, e.g., water.

According to some demonstrative embodiments of the invention, the entities may include microorganisms.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1:
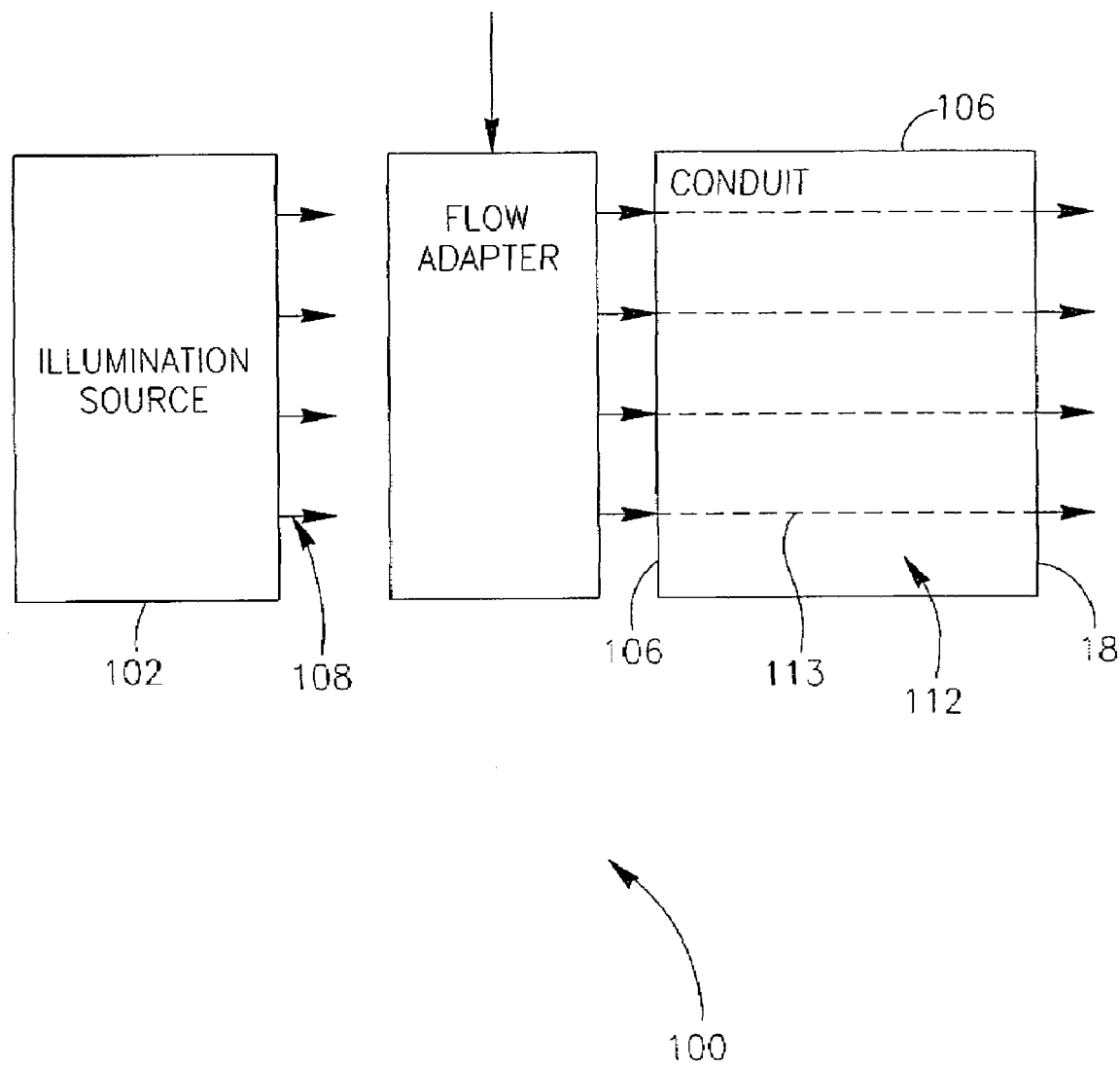
FIG. 1 is a conceptual illustration of an illumination-based disinfector according to some demonstrative embodiments of the invention.

It will be appreciated that for simplicity and clarity of illustration, elements shown in the drawings have not necessarily been drawn accurately or to scale. For example, the dimensions of some of the elements may be exaggerated relative to other elements for clarity or several physical components included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF EMBODIMENTS OF THE INVENTION

In the following detailed description, numerous specific details are set forth in order to provide a thorough understanding of the invention. However, it will be understood by those of ordinary skill in the art that the present invention may be practiced without these specific details. In other instances, well-known methods, procedures, components and circuits may not have been described in detail so as not to obscure the present invention.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices. In addition, the term "plurality" may be used throughout the specification to describe two or more components, devices, elements, parameters and the like.

Some demonstrative embodiments of the invention include a device, system and/or method to illuminate a medium having entities suspended therein, e.g., to disinfect the medium, as described in detail below.

It will be appreciated that the term "medium" as used herein may refer to any substance and/or matter, e.g., including water or air, which may be, for example, intended to be disinfected. The medium may be in any suitable thermodynamic state, e.g., liquid.

It will be appreciated that the term "entity" as used herein may refer to any organism, bacteria, microorganism, being, creature, microbe, germ, virus, organic contaminator, non-organic contaminator, oxidizable toxic or contaminator; any cumulative noxious species of biological or chemical origin; any oxidizing particle, fragment or element, e.g., Hydrogen peroxide or Titanium dioxide, intended to oxidize a contaminator; and/or the like. It will be appreciated that the phrase "entities suspended in a medium" as used herein may refer to any entity which may be suspended, contained, or mixed in the medium; and/or carried by the medium.

In some demonstrative embodiments of the invention, the device may include a conduit, for example, a chamber, e.g., an elongated chamber, to carry the medium. The conduit may have an inlet to receive the medium and an outlet to discharge the medium. The device may also include an illumination source to illuminate the conduit with light having a customized spatial light flux distribution corresponding to a plurality of optical tracks, having a plurality of optical track lengths, respectively, e.g., as described in detail below.

In some demonstrative embodiments of the invention, the customized light flux distribution may be based at least in part on an intended distribution of flow velocities of the entities suspended in the medium along a plurality of intended flow tracks from the inlet to the outlet, e.g., as described in detail below.

It will be appreciated that the term "flow track" as used herein may refer to a course, route, way, trail and/or track between two or more locations. For example, one or more of the entities suspended within the medium may travel along one or more flow tracks between a first location, e.g., the inlet of the conduit, and a second location, e.g., the outlet of the conduit. It will be appreciated that the phrase "intended flow track" as used herein may refer to a determined, computed, calculated, simulated, modeled, estimated, anticipated, assessed, assigned and/or planned flow track.

It will be appreciated that the phrase "intended distribution of flow velocities of entities along a plurality of intended flow tracks" as used herein may refer to a determined, calculated, computed, simulated, modeled, estimated, anticipated, assessed, planned, and/or assigned distribution, function, and/or profile, e.g., a probability distribution, function, and/or profile, of flow velocities of the entities along the intended flow tracks.

In some demonstrative embodiments of the invention, the device may remove at least part, e.g., substantially most or even all of the entities suspended in the medium. In some embodiments of the invention, the device may activate most or even all of oxidizing particles suspended within the medium.

Some demonstrative embodiments of the invention, e.g., as described below, may refer to using Ultra-Violet (UV) light to illuminate the medium, e.g., to disinfect the medium, and/or to oxidize the particles within the medium. However, it will be appreciated by those skilled in the art, that in other embodiments of the invention, light of any other suitable spectrum may be used.

Some demonstrative embodiments of the invention, e.g., as described below, may refer to illuminating water or a water-based medium, e.g., syrup. However, it will be appreciated by those skilled in the art, that other embodiments of the invention, may be implemented for illuminating any other suitable medium, e.g., air.

Reference is now made to FIG. 1, which conceptually illustrates an illumination-based disinfector 100 according to some demonstrative embodiments of the invention.

According to some demonstrative embodiments of the invention, disinfector 100 may include a conduit 106 to carry a flowing medium to be disinfected. Conduit 106 may have an inlet 116 to receive the medium, and an outlet 118 to discharge the medium.

According to some demonstrative embodiments of the invention, disinfector 100 may also include a flow adapter 104 configured to adapt a flow of the medium, e.g., at inlet 116, based on an intended distribution of flow velocities of entities suspended in the medium along a plurality of intended flow tracks 112, e.g., as described in detail below. The plurality of flow tracks 112 may include J flow tracks, e.g., from inlet 116 to outlet 118.

According to some demonstrative embodiments of the invention, disinfector 100 may also include an illumination source 102 to illuminate conduit 106 with light having a customized spatial light flux distribution, denoted $\Phi(x, y, z)$, wherein x, y, and z denote co-ordinates of locations within conduit 106. The spatial distribution $\Phi(x, y, z)$ may be based at least in part on the intended spatial distribution of flow velocities, e.g., as described in detail below. Although the invention is not limited in this respect, illumination source 102 may generate UV light of a suitable UV spectrum. For example, illumination source may include one or more UV lamps, e.g., a medium-pressure UV lamp, a high-pressure UV lamp, and/or a microwave UV lamp, as are all known in the art. Illumination source 102 may be external to conduit 106, e.g., as described below.

According to some demonstrative embodiments of the invention, an entity traveling through conduit 106 via an i-th track 113 of tracks 112, i=1 . . . J, may accumulate an illumination-dose resulting from the customized light flux distribution. The accumulated illumination-dose may be expressed, for example, in terms of fluency, e.g., energy/area. The illumination-dose accumulated by the entity may depend on one or more attributes of the entity, conduit 106, and/or illumination source 102. For example, the illumination-dose accumulated by the entity may depend on a relation between the light flux distribution $\Phi(x, y, z)$ and a velocity of the entity along track 113, as described in detail below. Accordingly, a distribution of illumination-doses accumulated by the entities traveling through conduit 106 ("the cumulated illumination-dose distribution") may be related to one or more attributes of flow tracks 112. For example, entities traveling along different tracks may accumulate different illumination-doses, e.g., as described below.

It will be appreciated by those of ordinary skill in the art, that a probability of inactivating the entity flowing along track 113 ("the kill probability") may be related to the illumination-dose accumulated by the entity. A higher illumination-dose may result in a higher kill probability. Accordingly, an inactivation rate of disinfector 100 may depend on the cumulated illumination-dose distribution.

According to some demonstrative embodiments of the invention, one or more performance attributes of disinfector 100, e.g., an overall log-inactivation rate ("kill rate") of disinfector 100, may be affected by the cumulated illumination-dose distribution within conduit 106. For example, the performance attributes of disinfector 100 may be limited by one or more low-illumination-dose flow tracks. Thus, a narrow illumination-dose distribution may result in a better disinfection ability of disinfector 100. Therefore, it may be desired to configure flow adapter 104, illumination source 102, and/or conduit 106 based on a desired, e.g., relatively narrow, illumination-dose distribution, as described in detail below.

According to some demonstrative embodiments of the invention, the medium entering conduit 106 at inlet 116 may include $m_v$ entities per unit volume. For simplicity, it may be assumed that the distribution of the entities is substantially spatially uniform at inlet 116. However the invention is not limited in this respect and it will be appreciated by those of ordinary skill in the art, that other embodiments of the invention may be implemented with regard to a non-uniform distribution of the entities.

Although the invention is not limited in this respect, it may be assumed that the velocity of the entities is equal to the velocity of the medium carrying the entities along tracks 112, i.e., it may be assumed that there is substantially no relative drag and/or substantially no differential obstacle.

According to some demonstrative embodiments of the invention, an area, denoted A, of inlet 116 (not shown) may be divided into a plurality of cross-sectional cells. For example, the area A may be divided into J equal cells, each having a size $\Delta A = A/J$. Track 113 may have a characteristic length, denoted $l_i$, and a characteristic crossing time, denoted $T_i$, at which the entities of track 113 travel from inlet 116 to outlet 118.

According to some demonstrative embodiments of the invention, it may be assumed that a size of the i-th cell may remain substantially constant along track 113, e.g., since it may be assumed that a cross sectional area of a volume of the medium may remain substantially constant along the track from inlet 116 to outlet 118. However, it will be appreciated by those of ordinary skill in the art that the invention is not limited in this respect, and that other embodiments of the invention may relate any other suitable cell arrangement, e.g., having cells including a specific mass of the medium, or cells including a specific number of entities. These other embodiments may be implemented, for example, in relation to disinfectors wherein the cross-sectional area of the volume of the medium may vary along the track, e.g., if inlet 116 and outlet 118 have different cross-sectional areas.

According to some demonstrative embodiments of the invention, a total number of entities, denoted $M_i$, traveling along track i through conduit 106 during a time period, denoted T, may be determined as follows:

$$M_i = m_v \cdot (\Delta A) \cdot T \cdot \frac{l_i}{T_i} \equiv m_v \cdot (\Delta A) \cdot T \cdot V_i \quad (1)$$

wherein $V_i$ denotes an average velocity of crossing the reactor through the i-th track.

According to some demonstrative embodiments of the invention, a total number of entities, denoted $N_{M-total}$, crossing conduit 106 during the time T may be determined as follows:

$$N_{M-total} = \sum_1^J M_i = m_v \cdot (\Delta A) \cdot T \cdot \sum_1^J \frac{l_i}{T_i} = m_v \cdot (\Delta A) \cdot T \cdot \sum_1^J V_i \quad (2)$$

Alternatively, the number $N_{M-total}$ may be determined based on a throughput, denoted Q, e.g., in terms of volume/time, of the medium through conduit 106, e.g., as follows:

$$N_{M-total} = m_v \cdot Q \cdot T \quad (3)$$

An average crossing velocity, denoted $V_{average}$, of tracks 112 may be determined, for example, as follows:

$$V_{average} = \frac{1}{J} \cdot \sum_1^J \frac{l_i}{T_i} = \frac{1}{J} \cdot \sum_1^J V_i \quad (4)$$

Assuming the velocity of the entities is substantially equal to the velocity of the medium, the throughput Q may be determined as follows:

$$Q = A \cdot V_{average} \quad (5)$$

It will be appreciated that Equation 2 may be derived by inserting Equations 4 and 5 into Equation 3.

Relating to Equations 1 and/or 2, it will be appreciated that flow tracks 112 may be weighted by the respective average velocities $V_i$, for example, since a "faster" track having a higher value $V_i^1$ may carry a larger number of entities across conduit 106, compared to a "slower" track having a lower value of $V_i^2$.

In some demonstrative embodiments of the invention, e.g., as are described herein, affects of turbulence within conduit 106 may be neglected. However, it will be appreciated by those of ordinary skill in the art that the invention is not limited in this respect, and the embodiments of the invention described herein may be modified to take into account turbulent flow, which may affect, for example, the illumination-dose distribution. For example, it will be appreciated that the illumination-dose distribution may be narrowed, e.g., if the flow through conduit 106 is characterized by relatively high Reynolds numbers.

According to some demonstrative embodiments of the invention, the entity traveling along track 113 may "accumulate" an illumination-dose, denoted Dose(track$_i$), which may be expressed in terms of energy/area. The accumulated illumination dose of the track i may include a cumulative light-velocity ratio corresponding to the track i, and including a sum of ratios related to the track i. The sum of ratios may include a sum of ratios between intended light intensities resulting from the customized light flux at a plurality of locations along the path and intended flow velocities at the plurality of locations. The accumulated illumination-dose may be determined, for example, as follows:

$$Dose(track_i) = \int_{track-i} \Phi(x, y, z) \cdot dt = \int_{track-i} \frac{\Phi(x, y, z)}{|V_i(x, y, z)|} \cdot dl \quad (6)$$

wherein dt denotes a time required to cross a track increment of length dl; and $|V_i(x, y, z)|$ denotes a magnitude of the velocity of the entity at the location (x,y,z).

Although the invention is not limited in this respect, according to some demonstrative embodiments of the invention, the light distribution flux at a certain point within conduit 106 may be evaluated, for example, by using a detailed ray-tracing algorithm, and summing-up rays reaching the certain point, e.g., as described below with reference to FIGS. 18A-22C. The light distribution flux may depend, for example, on a configuration of conduit 106, a configuration of light source 102, and/or one or more attributes, e.g., transmission, of the medium, as described in detail below.

Although the invention is not limited in this respect, according to some demonstrative embodiments of the invention, the velocity $|V_f(x, y, z)|$ may be evaluated, for example, using any suitable computerized fluid dynamic (CFD) technique and/or algorithm, e.g., assuming the entities are "passively" carried by the medium at a speed substantially identical to the speed of the medium, e.g., as described below.

Referring to Equation 1, the length $l_i$ and/or the crossing time $T_i$ relating to the i-th track may be evaluated, for example, as follows:

$$l_i = \int_{track-i} dl \quad (7)$$

$$T_i = \int_{track-i} \frac{dl}{|V_f(x, y, z)|}$$

A dose distribution function, e.g., in the form of a histogram, may represent a number of entities crossing conduit 106, e.g., per unit time, which accumulated a certain illumination-dose value within a predefined illumination-dose "window", e.g., relative to a total number of entities that crossed conduit 106 during the unit time.

According to some demonstrative embodiments of the invention, a normalized dose distribution function, denoted u(D), may be measured in terms of 1/Dose, e.g., area/energy. For example, the function u(D) may be determined as follows:

$$u(D) = \frac{N_M(D)}{\int_{D_{min}}^{D_{max}} N_M(D) \cdot dD} \quad (8)$$

wherein $N_M(D)$ denotes the number of entities traveling through tracks having an illumination-dose of between D and D+dD; $D_{min}$ denotes a minimal illumination-dose along tracks 112; $D_{max}$ denotes a maximal illumination-dose along tracks 112; and wherein u(D) satisfies the following equation:

$$\int_{D_{min}}^{D_{max}} u(D) \cdot dD = 1 \quad (9)$$

According to some demonstrative embodiments of the invention, a number, denoted $N_M$, of "surviving" entities at outlet 118 may be determined as follows, e.g., assuming an exponential decay rate of the entities in response to the illumination-dose resulting from the light generated by illumination source 102:

$$N_M = N_{M-total} \cdot \int_{D_{min}}^{D_{max}} u(D) \cdot e^{-a \cdot D / D_{1log}} \cdot dD \quad (10)$$

wherein a denotes a predefined constant, for example, a=ln (10)=2.3; and wherein $D_{1log}$ denotes an illumination-dose required to achieve one-log inactivation of the entities.

For a "delta" dose distribution function, Equation 10 may describe a straight line in a log-inactivation vs. UV-dose plane. Other dose distribution functions may have a sub-linear log-inactivation vs. UV-dose curve, i.e., a curve "bending down" at high illumination-dose values, e.g., as described below. Such sub-linear curve may be referred to as a "shouldered survival curve".

In some demonstrative embodiments of the invention, e.g., as described herein, it may be assumed that all entities flowing through the conduit have a single-resistivity, i.e., substantially the same accumulated illumination dose is required for killing/eliminating all the entities. However the invention is not limited in this respect and it will be appreciated by those of ordinary skill in the art, that other embodiments of the invention may be implemented with regard to entities of a multi-resistivity.

A track average dose may be defined as follows:

$$D_{av} = \int_{D_{min}}^{D_{max}} D \cdot u(D) \cdot dD \quad (11)$$

A calculated equivalent dose, denoted $D_{eq}$, may be defined as an illumination dose required to achieve the number of surviving entities $N_M$ in accordance with Equation 10, e.g., assuming a single dose value to all tracks 112 (a "delta-function" distribution). The dose $D_{eq}$ may be determined, for example, as follows:

$$D_{eq} = -\frac{D_{1log} \cdot \ln[N_M / N_{M-total}]}{a} \quad (12)$$

According to some demonstrative embodiments of the invention, a track-uniformity factor, denoted $U_f$, may be defined as follows:

$$U_f \equiv \frac{D_{eq}}{D_{av}} \quad (13)$$

It will be appreciated that the calculated equivalent dose may be equal to or smaller than the track average Dose, i.e., $D_{eq} \leq D_{av}$. The calculated equivalent dose may be equal to the track average dose, for example, for the delta dose distribution function, i.e., if a single illumination-dose value is accumulated by entities at each track. Accordingly, the track-uniformity factor may satisfy:

$$0 \leq U_f \leq 1 \quad (14)$$

The value of $U_f$ may represent an efficiency level of disinfector 100, e.g., a low value of $U_f$ may represent a low efficiency level of disinfector 100.

Equation 13 may be rearranged as follows:

$$D_{eq} = U_f D_{av} \quad (15)$$

Therefore, the equivalent dose may be calculated based on the value of the track-uniformity factor and the track-average dose, e.g., using Equation 15.

Following, are examples relating to illumination-dose distribution functions in accordance with some demonstrative embodiments of the invention. It should be noted that the illumination-dose distribution functions used in these examples are not intended to limit the scope of the invention to any particular disinfector configuration and/or illumination-dose distribution function.

Figure 2:
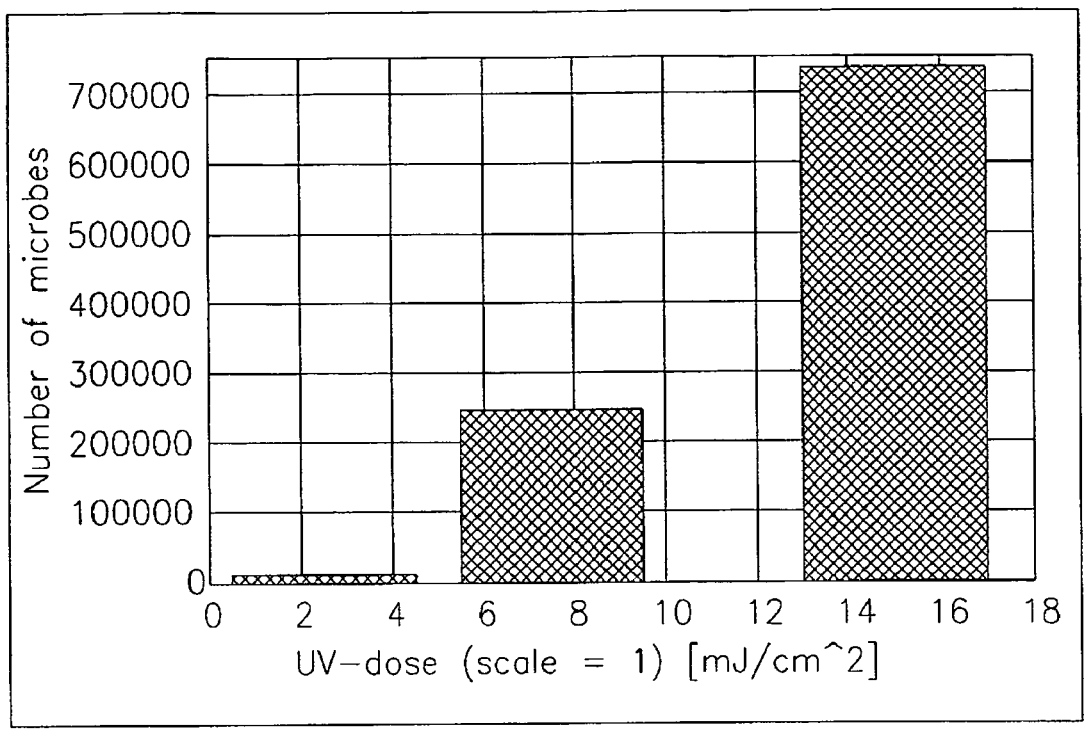
FIG. 2 is a schematic illustration of an illumination-dose distribution function according to one demonstrative embodiment of the invention.

According to a first example, the illumination-dose distribution function may include three dose zones. For example, tracks 112 may be divided into three groups, namely, a low-dose group, a medium-dose group and a high-dose group. According to this example, during the time T a total population of one million entities may travel through conduit 106. As shown in FIG. 2 and summarized in the following table, the low-dose group may include one percent of the entities, which may accumulate 0.5 of a certain illumination-dose value, e.g., $0.5*D_{1log}$; the medium-dose group may include twenty-five percent of the entities, which may accumulate 1.5 times the certain illumination dose value, e.g., $1.5*D_{1log}$; and the high-dose group may include seventy-four percent of the entities, which may accumulate 3 times the certain illumination-dose value, e.g., $3*D_{1log}$, wherein, for example, $D_{1log}=5$ mJ/cm$^2$.

TABLE 1

|  | Low-Dose group | Medium-Dose Group | High-Dose Group |
|---|---|---|---|
| Relative number Of microbes in group | 1/100 | 25/100 | 74/100 |
| Relative Dose | 0.5 | 1.5 | 3 |

Figure 3:
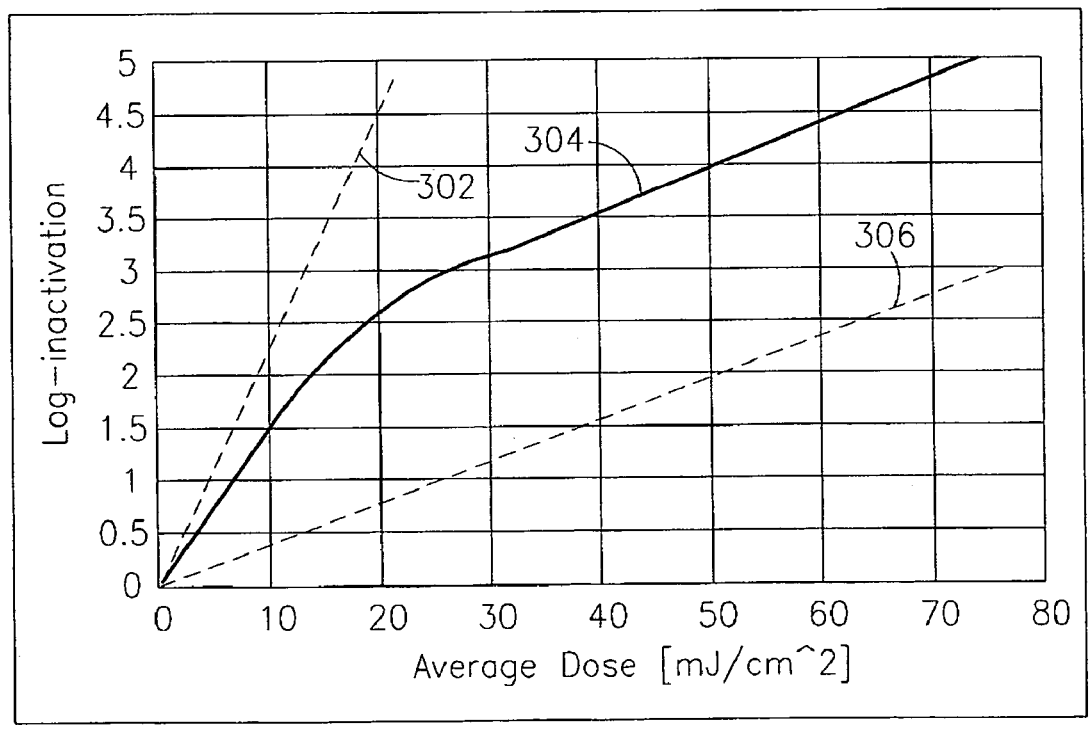
FIG. 3 is a schematic illustration of a graph depicting first, second, and third curves of the log-inactivation versus the track-average dose, resulting from the illumination-dose distribution function of FIG. 2.

FIG. 3 schematically illustrates a graph depicting first, second, and third curves denoted 304, 302, and 306, respectively, of the log-inactivation (kill rate) resulting from the total population, the high-dose group, and the low-dose group, respectively, versus the track-average dose. As shown in FIG. 3, at very low track-average dose levels the kill rate may be dominated by the kill rate of entities in the high-dose group (curve 302). The kill rate may be increased, e.g., from 2-log to 4-log, by increasing the track-average dose, e.g., from about 15 mJ/cm$^2$ to about 50 mJ/cm$^2$. The track-average dose may be increased, for example, by increasing the light output power of illumination source 102 (FIG. 1), decreasing the flow-rate of the medium through conduit 106 (FIG. 1), and/or the medium being of higher quality, as discussed below.

As also shown in FIG. 3, as the track-average dose level increases, the kill-rate may be generally dominated by the kill rate of entities in the low-dose group (curve 306), e.g., since, most of the entities in the high-dose group have already been inactivated ("dead"). As further shown in FIG. 3, an increase in the track-average dose may result in a sub-linear increase in log-inactivation, e.g., due to the dose/track non-uniformity of the dose distribution.

Figure 4:
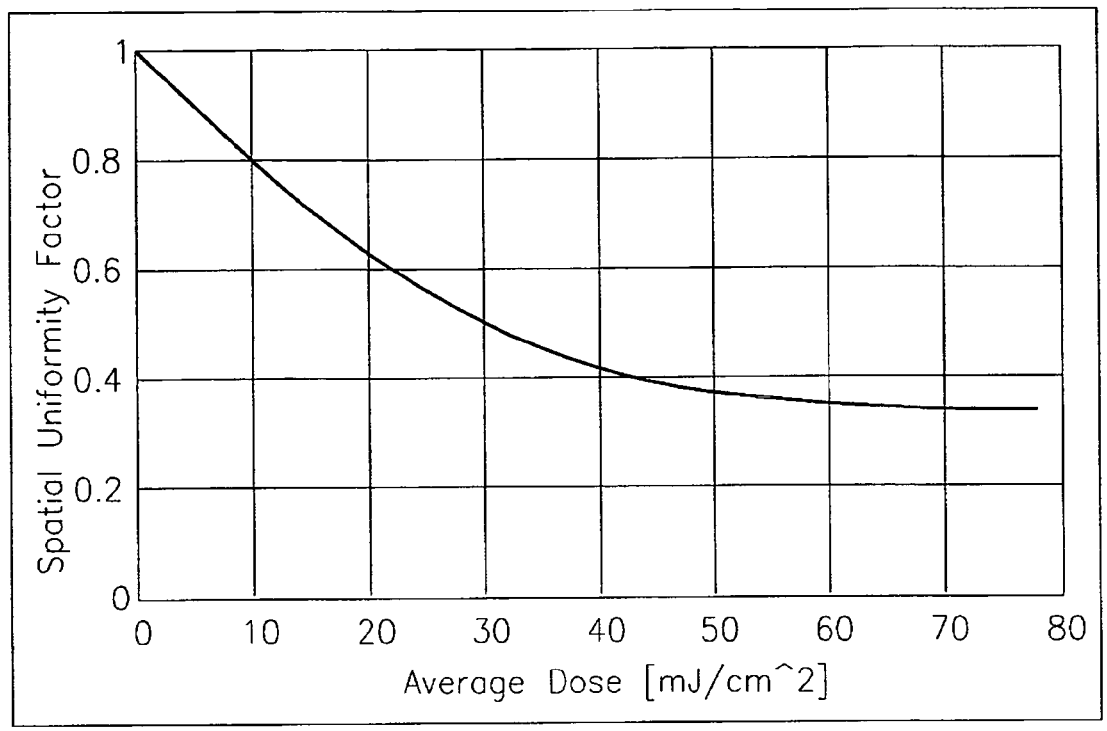
FIG. 4 is a schematic illustration of a graph depicting the track-uniformity factor versus the track average dose, resulting from the illumination-dose distribution function of FIG. 2.

FIG. 4 schematically illustrates a graph depicting the track-uniformity factor versus the track average dose, resulting from the illumination-dose distribution function of FIG. 2. As shown in FIG. 4, the value of $U_f$ may decrease from approximately 1 to approximately 0.3, as the dose values increase from approximately zero to approximately 80.

According to another example, the illumination-dose distribution may include a truncated-Gaussian distribution, which may be represented, for example, as follows:

$$u_G(D) = \begin{cases} \frac{A_0}{\sigma_D \cdot sqrt(2 \cdot \pi)} \cdot e^{-\frac{(D-\mu)^2}{2*\sigma_D^2}} & ; D_{min} \leq D \leq D_{max} \\ 0; \text{Otherwise} \end{cases} \quad (16A)$$

wherein $D_{min}$ denotes a lowest dose value in the dose distribution; $D_{max}$ denotes a highest dose value in the dose distribution; $\sigma_D$ denotes a width of the Gaussian distribution; $\mu$ denotes a center of the Gaussian distribution; $A_0$ denotes normalization constant, e.g., such that $u_G(D)$ satisfies Equation 9.

It is noted that if $A_0=1$, then $\mu$ may be equal to the track-average dose, and $\sigma_D$ may be equal to the standard deviation, if the Gaussian distribution is "narrow" relative to the following truncation values:

$$D_{max}-\mu >> \sqrt{2}\cdot\sigma_D \text{ and } \mu-D_{min} >> \sqrt{2}\cdot\sigma_D \quad (16B)$$

Figure 5:
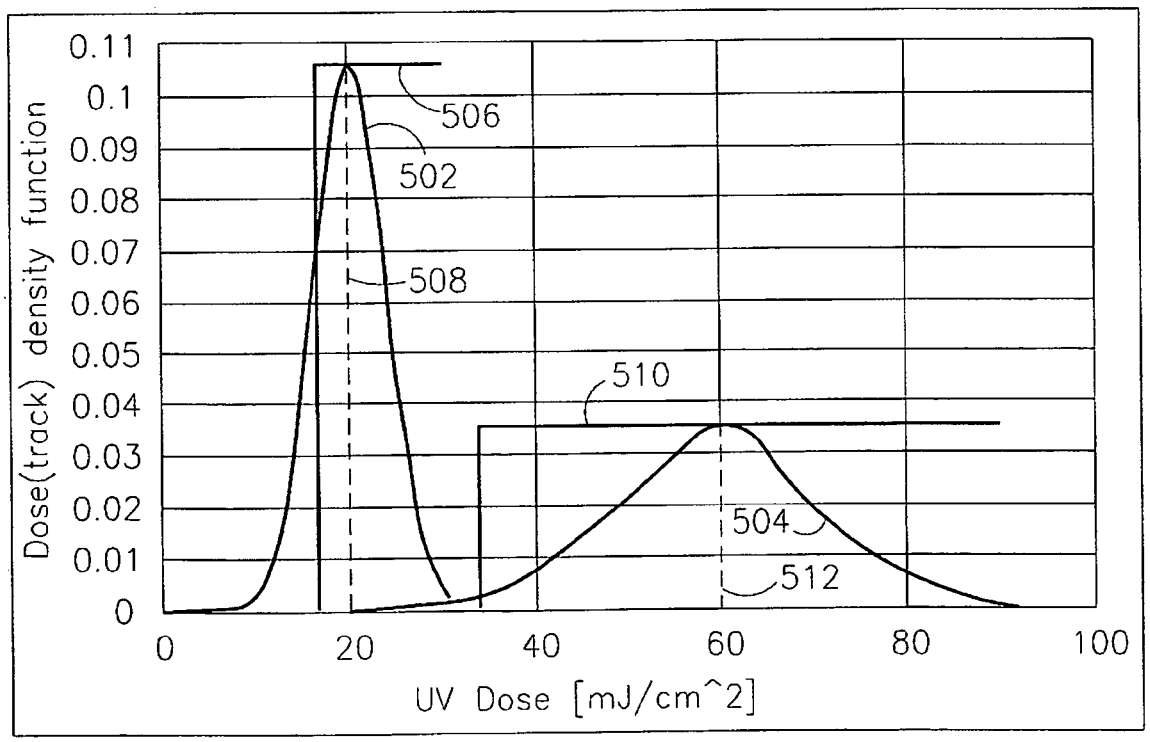
FIG. 5 is a schematic illustration of a graph depicting first and second Gaussian dose distribution curves according to a demonstrative embodiment of the invention.

FIG. 5 schematically illustrates a graph depicting first and second Gaussian dose distribution curves, denoted 502 and 504, respectively, according to a demonstrative embodiment of the invention. Both distribution curves 502 and 504 are defined by the following values, scaled by a common scale factor, denoted scale:

$D_{1log}=5$ mJ/cm$^2$ $D_{min}=0.7*D_{1log}*$scale $D_{max}=6*D_{1log}*$scale $\mu=4*D_{1log}*$scale $\sigma_D=0.75*D_{1log}*$scale wherein distribution curve 502 corresponds to the scale factor scale=1, and distribution curve 504 corresponds to the scale factor scale=3.

As shown in FIG. 5, the scale factor scale=3, may result in a wider dose distribution, compared to lower scale factor scale=1. The wider dose distribution may result in a lower track-uniformity factor, as discussed below. The graph of FIG. 5 also depicts curves 506 and 508 representing the track-average dose and calculated equivalent dose, respectively, corresponding to distribution curve 502; and curves 510 and 512 representing the track-average dose and calculated equivalent dose, respectively, corresponding to distribution curve 504. As shown in FIG. 5, it will be appreciated that the calculated equivalent dose may not "scale" with the track-average dose.

Figure 6:
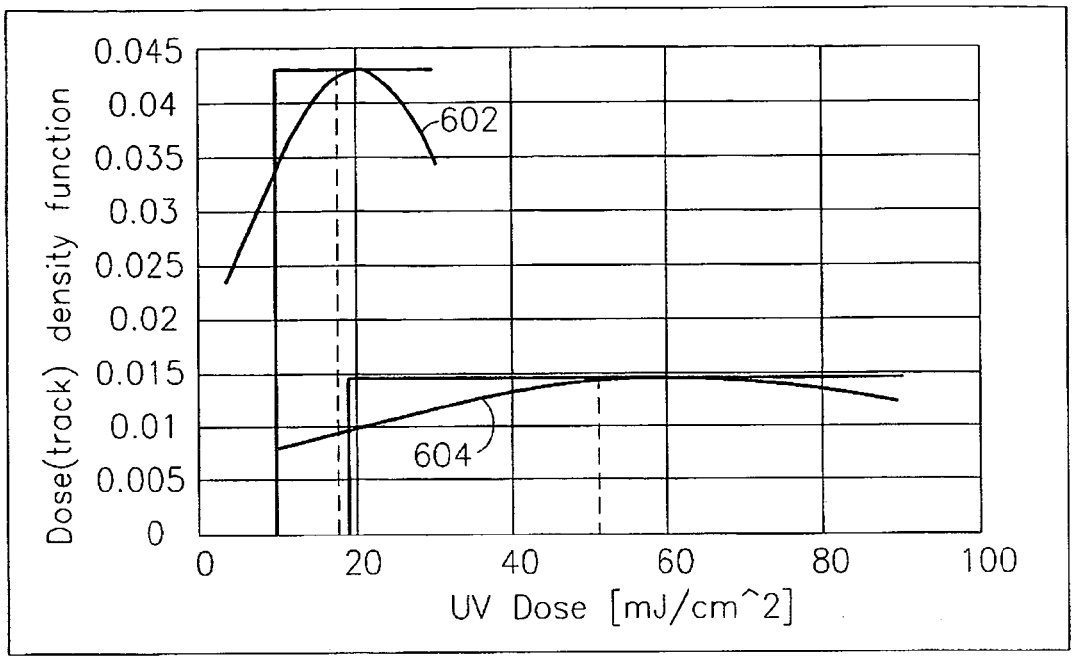
FIG. 6 is a schematic illustration of a graph depicting first and second Gaussian dose distribution curves according to another demonstrative embodiment of the invention.

FIG. 6 schematically illustrates a graph depicting first and second Gaussian dose distribution curves, denoted 602 and 604, respectively, according to another demonstrative embodiment of the invention. Both distribution curves 602 and 604 are defined by the following values, scaled by the scale factor:

$D_{1log}=5$ mJ/cm$^2$ $D_{min}=0.7*D_{1log}*$scale $D_{max}=6*D_{1log}*$scale $\mu=4*D_{1log}*$scale $\sigma_D=3*D_{1log}*$scale wherein distribution curve 602 corresponds to the scale factor scale=1, and distribution curve 604 corresponds to the scale factor scale=3.

Figure 7:
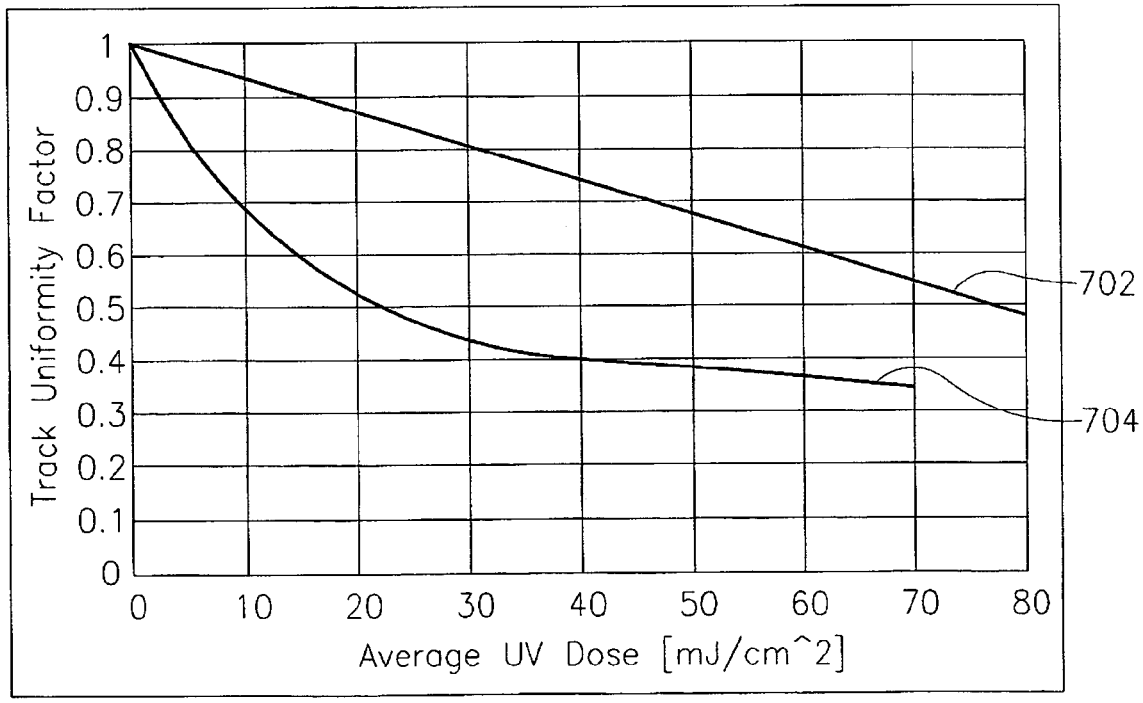
FIG. 7 is a schematic illustration of a graph depicting the track-uniformity factor versus the track average dose corresponding to distribution curves of FIGS. 5 and 6.

Reference is also made to FIG. 7, which schematically illustrates first and second curves, denoted 702 and 704, respectively, representing the track-uniformity factor versus the track average dose corresponding to distribution curves 502 and 602, respectively. As shown in FIG. 7, the value of the track-uniformity factor of curve 702 is generally above 0.5, e.g., even for relatively high values of the track average dose. Conversely, the value of the track-uniformity factor of curve 704 decreases when increasing the track-average dose, reaching values of less then 0.5 at relatively low values of the track average dose. Thus, a relatively wide dose distribution (e.g., corresponding to curve 502) may result in a steeper decrease in the track-uniformity factor, compared to the track-uniformity factor resulting from a relatively narrow dose distribution (e.g., corresponding to curve 602).

Figure 8:
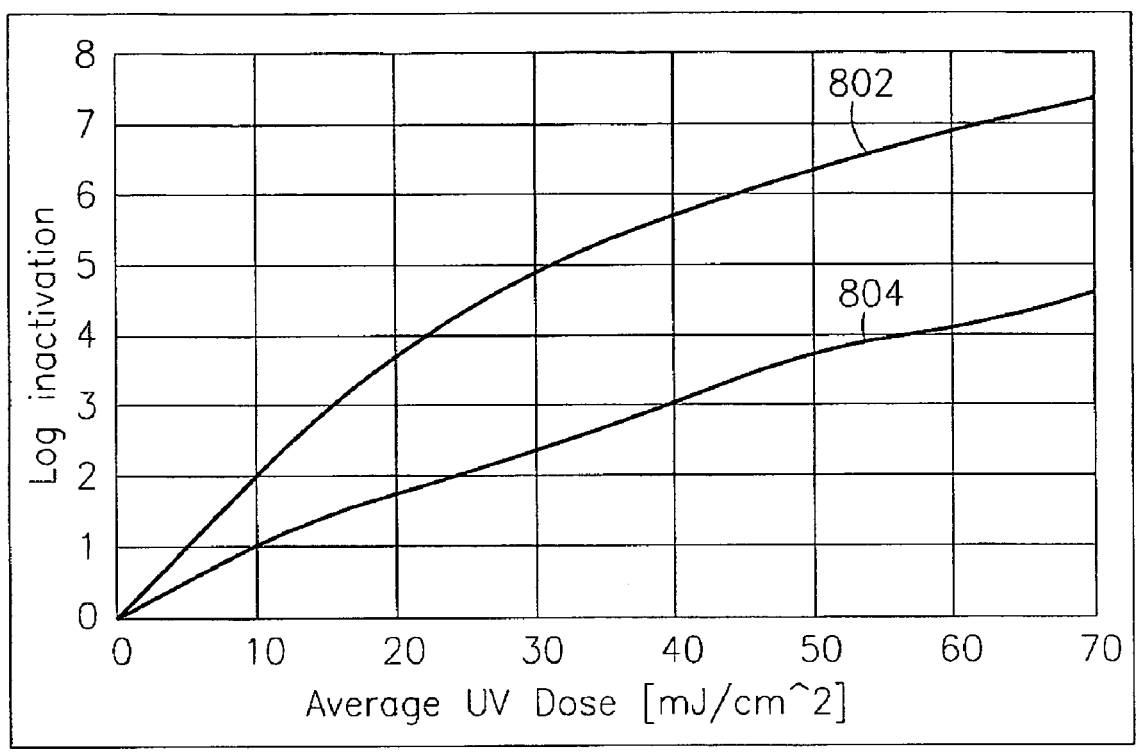
FIG. 8 is a schematic illustration of a graph depicting the kill rate versus the track average dose corresponding to distribution curves of FIGS. 5 and 6.

Reference is also made to FIG. 8, which schematically illustrates first and second curves, denoted 802 and 804, respectively, representing the kill rate versus the track average dose, corresponding to distribution curves 502 and 602, respectively. As shown in FIG. 8, the kill rate of curve 802 increases relatively sharply, reaching relatively high kill rates at high track-average dose values. Conversely, the kill rate of curve 804 "slows" down and bends "early", such that the log-inactivation values do not exceed 5, even at relatively high track-average dose values. Thus, a relatively narrow dose distribution (e.g., corresponding to curve 502) may result in a steeper increase in the kill rate, compared to a relatively wide dose distribution (e.g., corresponding to curve 602).

In another example analogous to the examples described above, a near-Gaussian Dose Distribution centered at Track-Average Dose of $4*Dose_{1log}$ and having a standard deviation of $2*Dose_{1log}$, may result in an overall kill rate of 2.25-log, and a Track-Uniformity Factor of 0.56. In this example, an overall kill rate of 4-log may be achieved, for example, by increasing the overall UV power by a factor of 2.6.

Referring back to FIG. 1, according to some demonstrative embodiments of the invention, an increase in the scale factor may be achieved by increasing the light output power of illumination source 112, decreasing the flow-rate of the medium through conduit 106, and/or using a medium of a higher quality, as discussed below.

According to some demonstrative embodiments of the invention, illumination source 102 may include a UV illumination source to illuminate conduit 106 with UV light. The track-average dose may be evaluated as follows, e.g., if disinfector 100 is characterized by a "delta" dose distribution function, i.e., wherein entities of substantially all tracks 112 accumulate the same illumination dose:

$$D_{av} = \frac{P_{0-germicidal}}{Flow} \cdot L_{effective}(UVT) \quad (17)$$

wherein $P_{0-germicidal}$ denotes a germicidal UV power in conduit 106 [energy/time]; Flow denotes a flow rate of the medium through conduit 106 [volume/time]; and $L_{effective}$ denotes an effective length of UV-rays illuminating conduit 106, e.g., depending on a geometry of conduit 106 and/or transmission-related characteristics of the medium.

According to Equation 17, an increase in the track-average dose may be achieved by increasing the UV power, decreasing the flow-rate, and/or increasing the effective length, e.g., using a medium of a higher quality.

According to some demonstrative embodiments, Equations 15 and 17 may be combined to yield the following Equation:

$$D_{eq} = U_f(P_{0-germicidal}, Flow, L_{effective}) \cdot \frac{P_{0-germicidal}}{Flow} \cdot L_{effective}(UVT) \quad (18)$$

It will be appreciated, that according to Equations 17 and/or 18 a linear increase of the track-average dose, e.g., by increasing the UV power, decreasing the flow-rate, and/or increasing the effective length, may not result in a linear increase in the log-inactivation, since the linear increase of the track-average dose may also result in a decrease in the track-uniformity factor, e.g., as discussed above. It is noted, that a simultaneous change of two or more of the parameters affecting the track-average dose, may result in a change in the calculated equivalent dose, e.g., because of the value of the track-uniformity factor may change, reflecting the change in the dose distribution function. For example, if one or more parameters of Equation 17 are simultaneously changed such that the track-average dose value remains substantially unchanged, e.g., by doubling the power and doubling the flow-rate, then the calculated equivalent dose, e.g., according to Equation 18, may still change. Accordingly, it may be desired to validate disinfector 100 at different power/flow/UVT combinations using a similar average dose value.

According to one demonstrative embodiment of the invention if, for example, a relatively small percentage of tracks 112, e.g., 1/1000 of tracks 112, are associated with a very small illumination dose, e.g., a zero UV-dose, ("low-dose tracks") then the resulting kill-rate of disinfector 100 may not exceed 3-log, e.g., even if illumination source 112 is activated to generate relatively high illumination energy, the medium has a relatively slow flow rate, and/or the medium is relatively clear. Therefore, it may be desired according to demonstrative embodiments of the invention to reduce, e.g., minimize, the percentage of low-dose tracks, e.g., in order to achieve high kill-rates, and/or a high-efficiency of disinfector 100. This may be achieved, for example, be a relatively narrow dose distribution function.

It will be appreciated that according to the embodiments described above, it may be desired to "match" between the light-flux field generated by illumination source 112, and the medium-velocity field within conduit 106. For example, illumination source 112 may be adapted to generate high UV-flux zones substantially coinciding with high velocity zones within conduit 106. Low-dose tracks, e.g., characterized by a high velocity of the medium and/or a low UV-flux, may be avoided. This may result, for example, in a narrow dose-distribution function, which may result in disinfector 100 operating at a relatively high efficiency level, and/or achieving relatively high kill-rates.

Although the invention is not limited in this respect, the width of the dose distribution function may be measured, for example, in terms of a ratio of a difference between an average of the cumulative illumination doses and a minimum of the cumulative illumination doses to the average cumulative illumination dose. For example, the ratio may be smaller than 0.7, e.g., smaller than 0.4.

Figure 9:
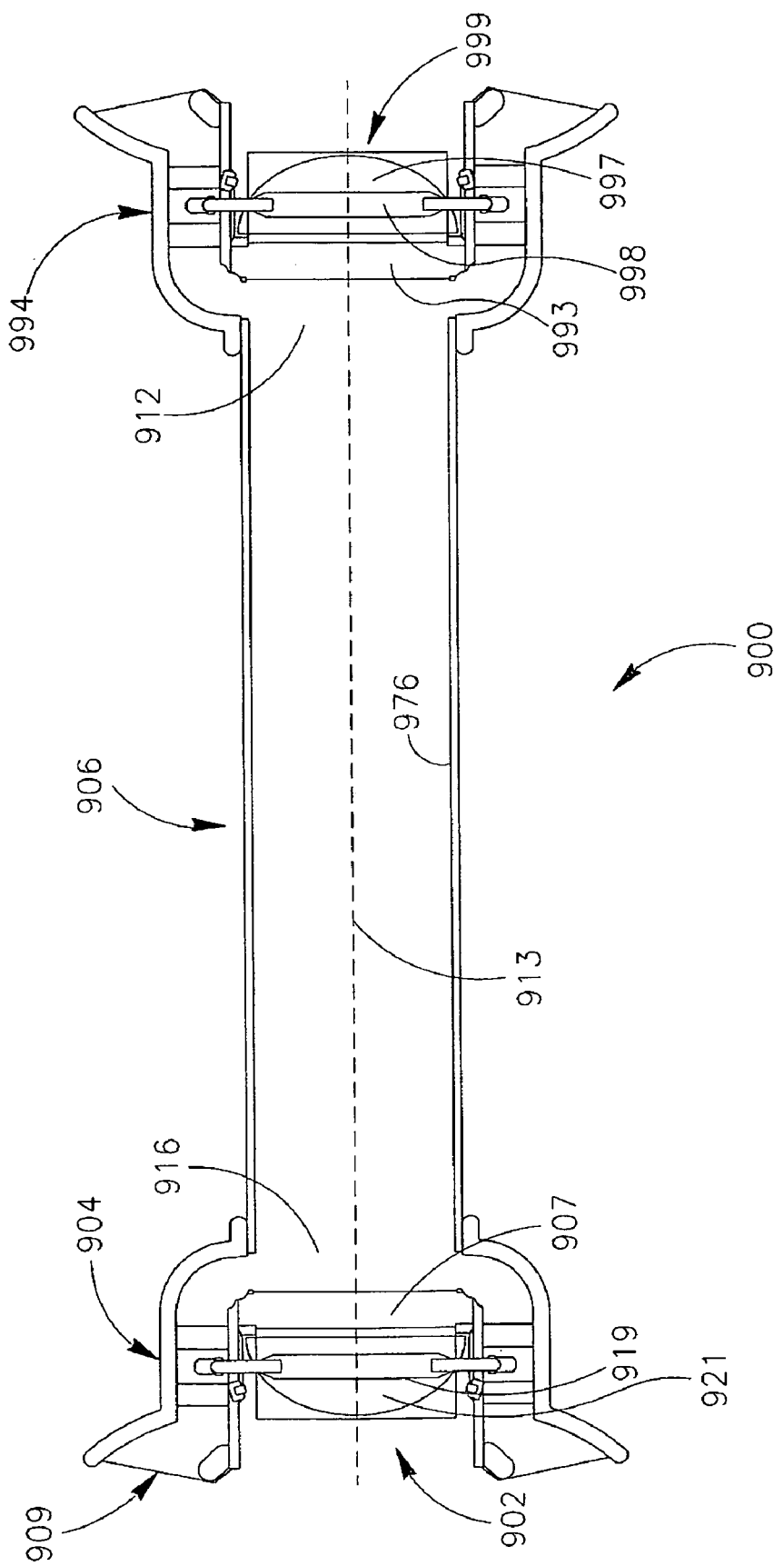
FIG. 9 is a schematic illustration of a disinfector including an external illumination source according to some demonstrative embodiments of the invention.

Reference is now made to FIG. 9, which schematically illustrates a disinfector 900 including an external illumination source 902 in accordance with some demonstrative embodiments of the invention. Although the invention is not limited in this respect, disinfector 900 may perform the functionality of disinfector 100 (FIG. 1), and/or illumination source 902 may perform the functionality of illumination source 102 (FIG. 1).

According to some demonstrative embodiments of the invention, disinfector 900 may also include a flow adapter 904, an elongated chamber 906, and a window 907, as are described in detail below. Although the invention is not limited in this respect, flow adapter 904 may perform the functionality of flow adapter 104 (FIG. 1), and/or chamber 906 may perform the functionality of conduit 106 (FIG. 1).

According to some demonstrative embodiments of the invention, flow adapter 904 may be configured to receive a medium at an inlet 909, and to provide the medium to an inlet 916 of chamber 906. Flow adapter 904 may be configured to adapt the flow of the medium provided to inlet 916 based on an intended spatial distribution of flow velocities of entities suspended in the medium along a plurality of intended flow tracks, e.g., from inlet 916 to an outlet 912 of chamber 906. Although the invention is not limited in this respect, flow adapter 904 may be cylindrically shaped, and/or chamber 906 may be tubular, wherein an inner diameter of adapter 904 may be larger than an inner diameter of inlet 916. It will be appreciated that this configuration may enable adapting the flow at inlet 916 such that at least part of the entities flowing along different tracks, e.g., substantially all the entities, have substantially the same velocity at inlet 916. In one demonstrative embodiment, flow adapter 904 and/or inlet 916 may be configured such that for a cylindrical chamber, the quantity of water flowing inward from a small angular segment around the chamber at a given unit time, may be substantially equal to the quantity of water flowing inward from another small angular segment around the chamber at the given unit time. For example, the inward flow rate may be substantially "cylindrically" symmetric.

Although the invention is not limited in this respect, in some embodiments the medium may include, for example, a liquid, e.g., water or a water based medium. Although the invention is not limited in this respect, in some embodiments the entities may include microorganisms.

According to some demonstrative embodiments of the invention, chamber 906 may be configured based at least in part on the intended distribution of flow velocities. For example, inlet 916 and/or outlet 912 may be configured based at least in part on the intended distribution of flow velocities.

Although the invention is not limited in this respect, according to some demonstrative embodiments of the invention, chamber 906 may include a quartz chamber, e.g., to enable Total Internal Reflection (TIR) of at least part of the light received from illumination source 902.

According to some demonstrative embodiments of the invention, illumination source 902 may be external to chamber 906. Window 907 may be located, for example, between illumination source 902 and inlet 916 to enable illumination source 902 to illuminate chamber 906.

According to some demonstrative embodiments of the invention, illumination source 902 and/or window 907 may be configured such that illumination source 902 may illuminate chamber 906 with light having a customized spatial light flux distribution. The customized light flux distribution may be based at least in part on the intended distribution of flow velocities within chamber 906, e.g., as described herein.

According to some demonstrative embodiments of the invention, the customized light flux distribution may result in an intended distribution of a plurality of cumulative light-velocity ratios corresponding to the plurality of flow tracks, respectively. One or more of the cumulative light-velocity ratios, e.g., each of the cumulative light-velocity ratios may include a sum, e.g., an integral, of ratios related to a respective track of the plurality of tracks. The sum of ratios may include, for example, a sum of ratios between intended light intensities resulting from the customized light flux at a plurality of locations along the track and intended flow velocities at the plurality of locations. For example, the plurality of cumulative light velocity ratios may include a plurality of accumulated illumination-doses Dose(track$_i$), e.g., according to Equation 6.

According to some demonstrative embodiments of the invention, the cumulative light-velocity ratios may have a relatively narrow intended distribution, e.g., as described above. For example, a ratio of a difference between an average of the cumulative illumination doses and a minimum of the cumulative illumination doses to the average cumulative illumination dose may be smaller than 0.7, e.g., smaller than 0.4.

According to some demonstrative embodiments of the invention, the intended distribution of flow velocities within chamber 906 may include a velocity profile, in which the velocity may decrease with an increase in the distance from a rotational axis 913 of chamber 906. For example, the velocity profile may have a maximum velocity value substantially at the rotation axis of chamber 906, and a minimum velocity value substantially at internal boundaries of chamber 906.

Figure 10:
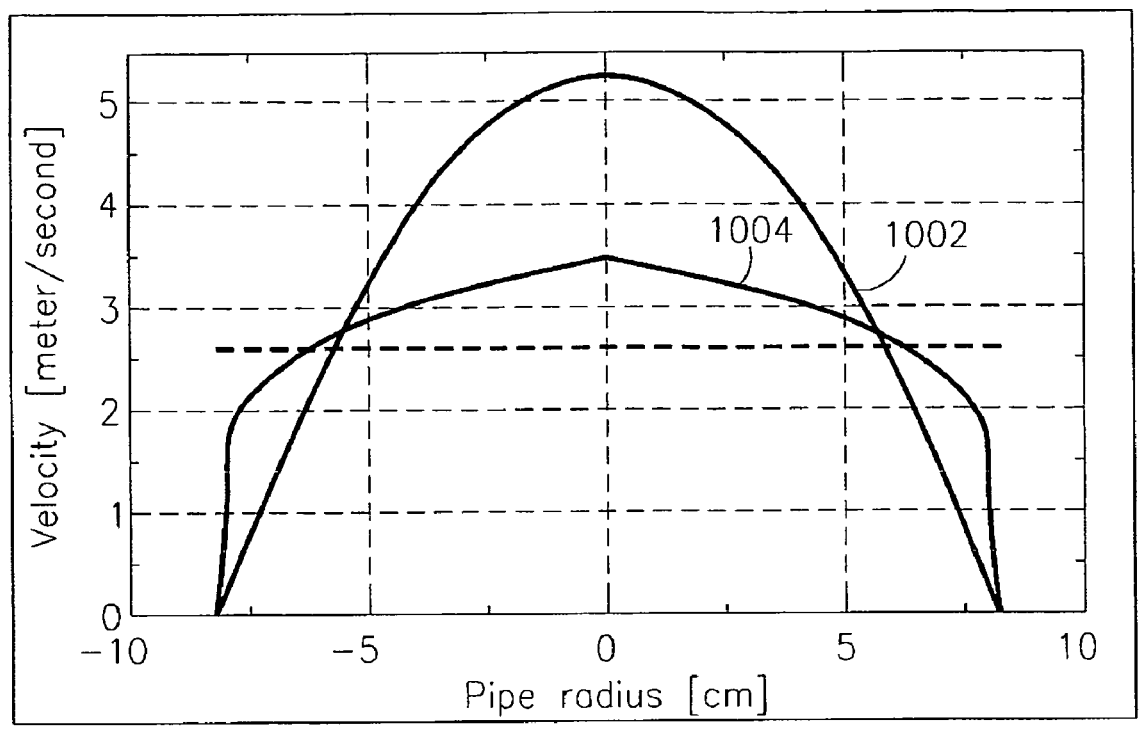
FIG. 10 is a schematic illustration of a graph depicting velocity versus distance from a chamber rotation-axis of a first velocity profile and a second velocity profile, according to some demonstrative embodiments of the invention.
Figure 11:
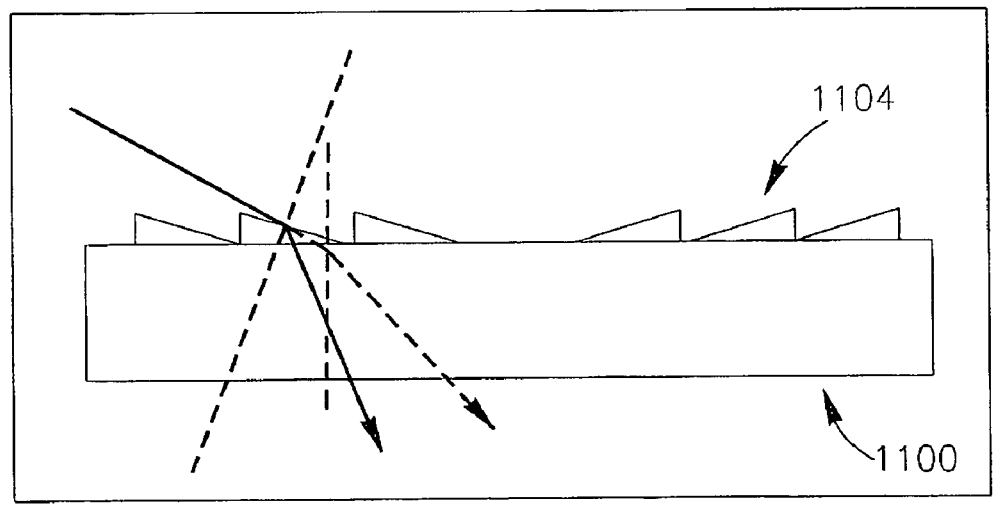
FIG. 11 is a schematic illustration of a window according to some demonstrative embodiments of the invention.

Reference is also made to FIG. 10, which schematically illustrates a graph depicting velocity versus distance from rotation-axis 913 of a first velocity profile 1002 and a second velocity profile 1004, according to some demonstrative embodiments of the invention. Velocity profile 1002 may correspond, for example, to a laminar flow within chamber 906, and velocity profile 1004 may correspond, for example, to a turbulent flow within chamber 906. As shown in FIG. 10, both profiles 1002 and 1004 have a maximal velocity value substantially at the rotation axis of chamber 906, which decreases with an increase in the distance from the rotation axis.

Referring back to FIG. 9, as discussed above, according to some demonstrative embodiments of the invention it may be desired to match between the distribution of flow velocities within chamber 906 and the customized light flux distribution, e.g., in order to achieve a relatively narrow intended distribution of the cumulative light-velocity ratios, which may result in an increased efficiency of disinfector 900 and/or a relatively high kill ratio. According to these embodiments, illumination source 902 and/or window 907 may be configured, e.g., as described below, such that a first intended light intensity resulting from the customized light flux at a first distance from rotation-axis 913 is smaller than a second intended light intensity resulting from the customized light flux at a second distance from rotation-axis 917, which is smaller than the first distance.

According to some demonstrative embodiments of the invention, the intended distribution of flow velocities within chamber 906 may include a velocity profile, in which a first velocity at a first distance from an inner surface 976 of chamber 906 may be smaller than a second velocity at a second distance from inner surface 976, which may be bigger than the first distance. According to these embodiments, illumination source 902 and/or window 907 may be configured, e.g., as described below, such that a first intended light intensity resulting from the customized light flux at the first distance is smaller than a second intended light intensity resulting from the customized light flux at the second distance.

According to some demonstrative embodiments of the invention, one or more optical attributes of window 907 may be based at least in part on the customized light flux distribution of illumination source 902. For example, a refractive index of window 907 in a spectrum of the light, e.g., the UV light, generated by illumination source 902. The one or more optical attributes of window 907 may be configured such that, for example, the light generated by illumination source 902 passes through window 907 to illuminate chamber 906 with light having substantially the customized light flux distribution, e.g., as described below.

Reference is also made to FIG. 1, which schematically illustrates a window 1100 according to some demonstrative embodiments of the invention. Although the invention is not limited in this respect, window 1100 may perform the functionality of window 907 (FIG. 9). Window 1100 may include one or more sections 1104 configured based on the customized light flux distribution.

Referring back to FIG. 9, according to some demonstrative embodiments of the invention, illumination source 902 may include at least one lamp 919 configured to generate light of a predefined distribution, and at least one reflector 921 to reflect at least part of the light generated by lamp 919 such that, for example, the light having the customized light flux distribution includes a combination of the light generated by lamp 919 and light reflected by reflector 921, e.g., as described below. Although the invention is not limited in this respect, lamp 919 may include, for example, a UV lamp to generate UV light.

According to some demonstrative embodiments of the invention, one or more attributes of reflector 921 may be based at least in part on one or more dimensions of chamber 906. For example, one or more attributes of reflector 921 may be based at least in part on an inner diameter of chamber 906, e.g., as described below.

Figure 12:
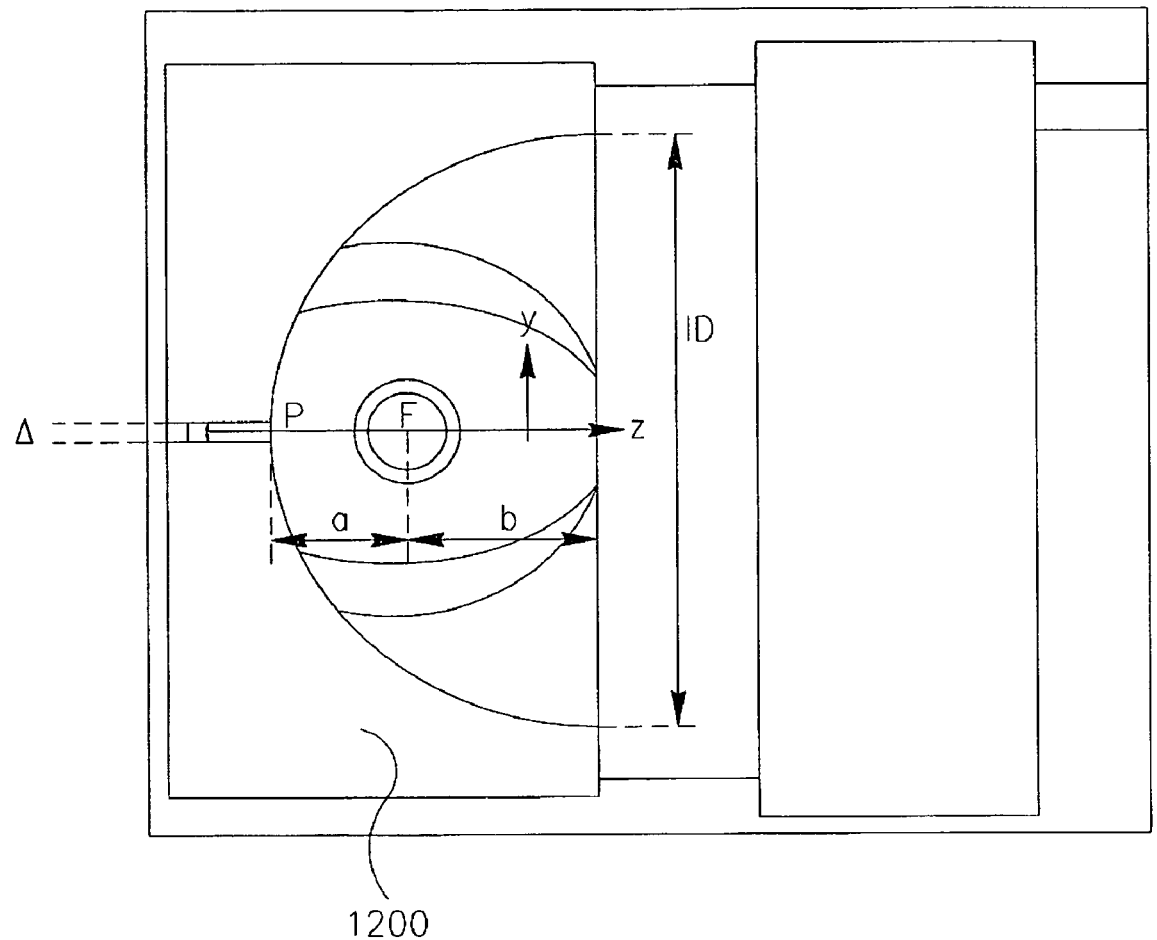
FIG. 12 is a schematic illustration of an elliptic reflector according to some demonstrative embodiments of the invention.

According to some demonstrative embodiments of the invention, reflector 921 may include an elliptic reflector. FIG. 12 schematically illustrates an elliptic reflector 1200 according to some demonstrative embodiments of the invention. Although the invention is not limited in this respect, reflector 1200 may have, for example, one or more of the following parameters:

ID=160.5 millimeter (mm);
R=67 mm;
Conic parameter=−0.32;
Δ=6.4 mm;
a=35.22 mm;
b=48.1 mm.

Although the invention is not limited in this respect, an elliptic reflector, e.g., reflector 1200, may be adapted for relatively high coupling efficiency and/or relatively uniform UV-dose distribution in an elongated tubular chamber, e.g., chamber 906, having an inner radius of, for example, about 164 mm.

Figure 13:
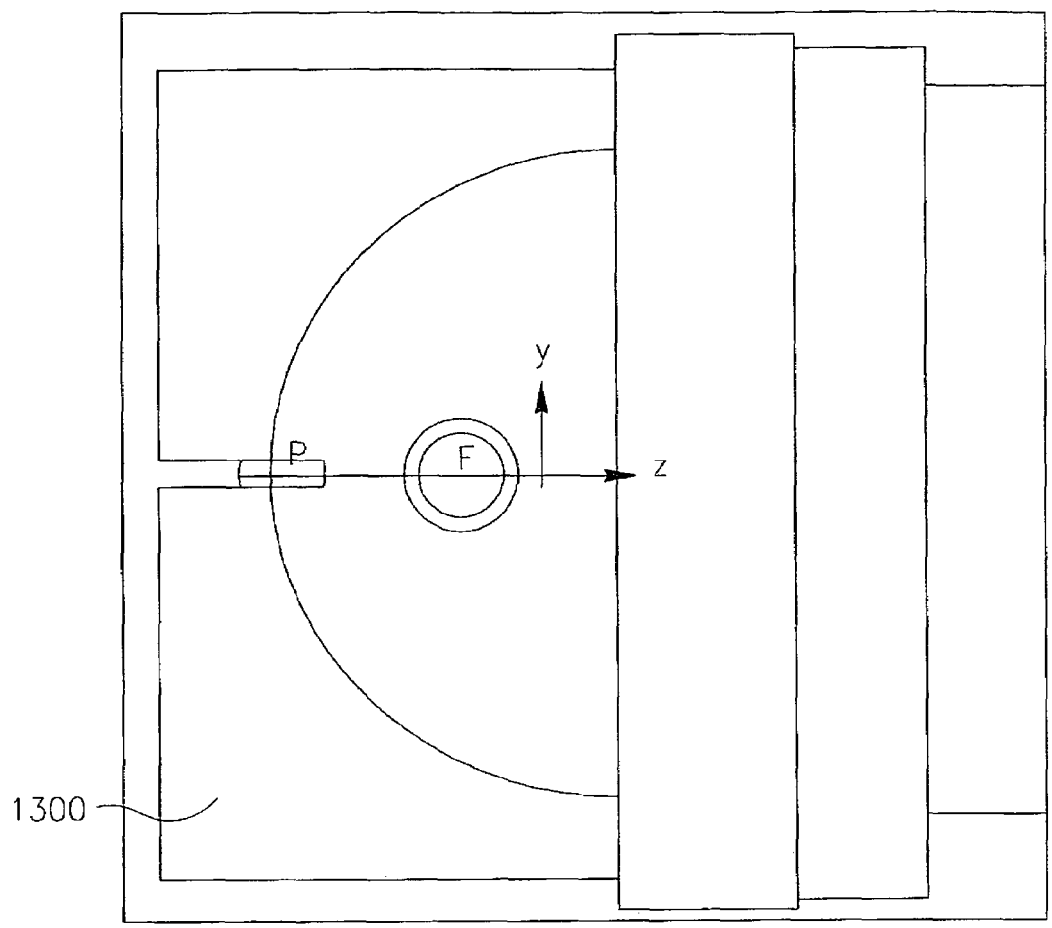
FIG. 13 is a schematic illustration of a spheroid reflector according to some demonstrative embodiments of the invention.

According to some demonstrative embodiments of the invention, reflector 921 may include a spheroid reflector. FIG. 13 schematically illustrates a spheroid reflector 1300 according to some demonstrative embodiments of the invention. Although the invention is not limited in this respect, reflector 1300 may have, for example, one or more of the following parameters:

D=160 mm;
Δ=6.4 mm;
a=52.8 mm;
b=27.2 mm.

Although the invention is not limited in this respect, a spheroid reflector, e.g., reflector 1300, may be adapted for relatively high coupling efficiency and/or relatively uniform UV-dose distribution in an elongated tubular chamber, e.g., chamber 906, having an inner radius of, for example, about 164 mm.

Figure 14:
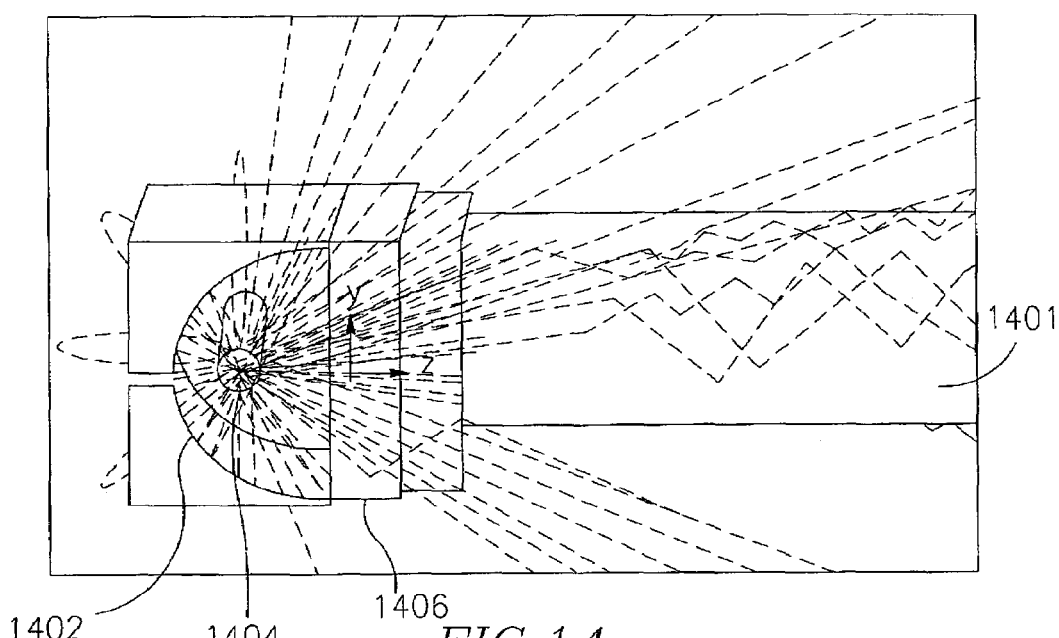
FIG. 14 is a schematic illustration of a computer simulation of a customized light flux distribution resulting from a combination of a reflector, lamp, and window according to one demonstrative embodiment of the invention.

According to some demonstrative embodiments of the invention, lamp 919, reflector 921, and/or window 907 may be configured to generate the customized light distribution in chamber 906. Any suitable algorithm, simulation, and/or method may be implemented to configure lamp 919, reflector 921, and/or window 907. FIG. 14 schematically illustrates a computer simulation of a customized light flux distribution in a chamber 1401 resulting from a combination of a reflector 1402, a lamp 1404, and a window 1406, according to one demonstrative embodiment of the invention.

According to some demonstrative embodiments of the invention, light source 902 and/or window 907 may be configured to generate a predefined light distribution at inlet 916, e.g., as described below.

Figure 15A:
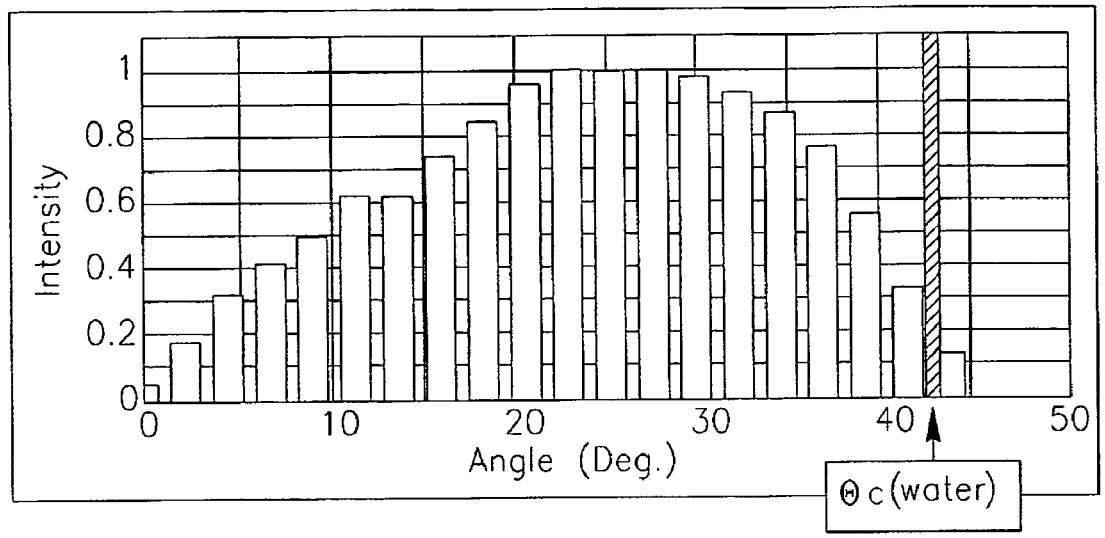
FIGS. 15A and 15B are schematic illustrations of first and second distribution histograms, respectively, each depicting light intensity versus axial angle of light rays at a chamber inlet, according to first and second, respective, embodiments of the invention.
Figure 15B:
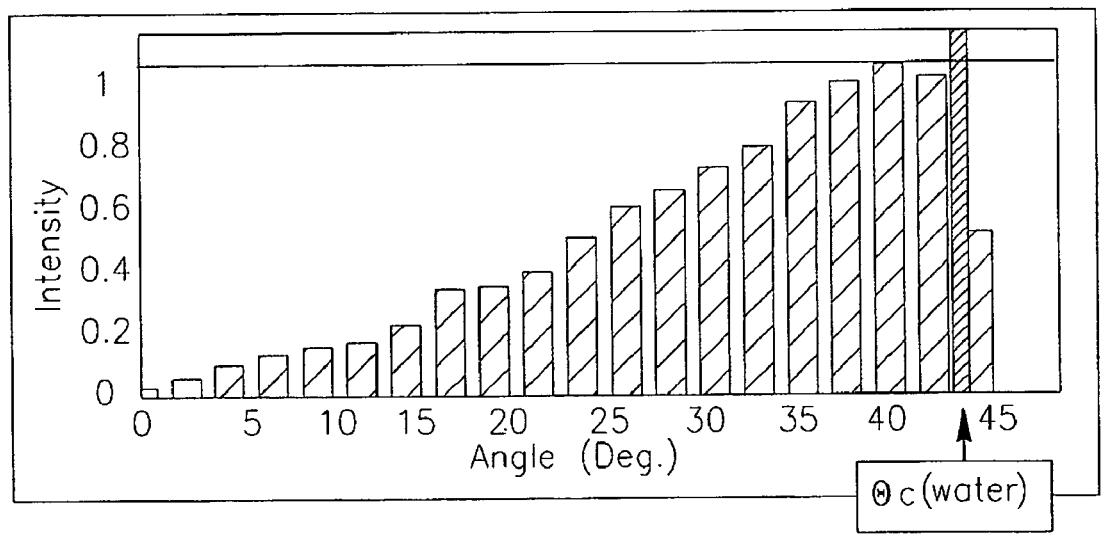

Reference is made to FIGS. 15A and 15B, which schematically illustrate first and second distribution histograms, respectively, each depicting light intensity versus axial angle of light rays at inlet 916, according to first and second, respective, embodiments of the invention. The distribution of FIG. 15A may result, for example, from an elliptic reflector, e.g., reflector 1200 (FIG. 12). The distribution of FIG. 15B may result, for example, from a spheroid reflector, e.g., reflector 1300 (FIG. 13). The distribution of FIG. 15A may include a majority of light rays having an angle smaller than a critical angle, denoted $\theta_c$, of total internal reflection within the medium to be disinfected. The critical angle may be, for example, $\theta_c \approx 42.6^\circ$, if, for example, the medium is water and chamber 906 is surrounded by air. It will be appreciated, that the light distribution of FIG. 15A may result in a relatively high coupling efficiency between the light rays and the entities flowing through chamber 906. The distribution of FIG. 15B may include light rays having relatively high axial angles, e.g., to achieve the customized flux distribution.

Referring back to FIG. 9, according to some demonstrative embodiments of the invention one or more sections of reflector 921 may be configured based on one or more local light flux distributions of the customized light flux distribution, e.g., as described below.

Figure 16:
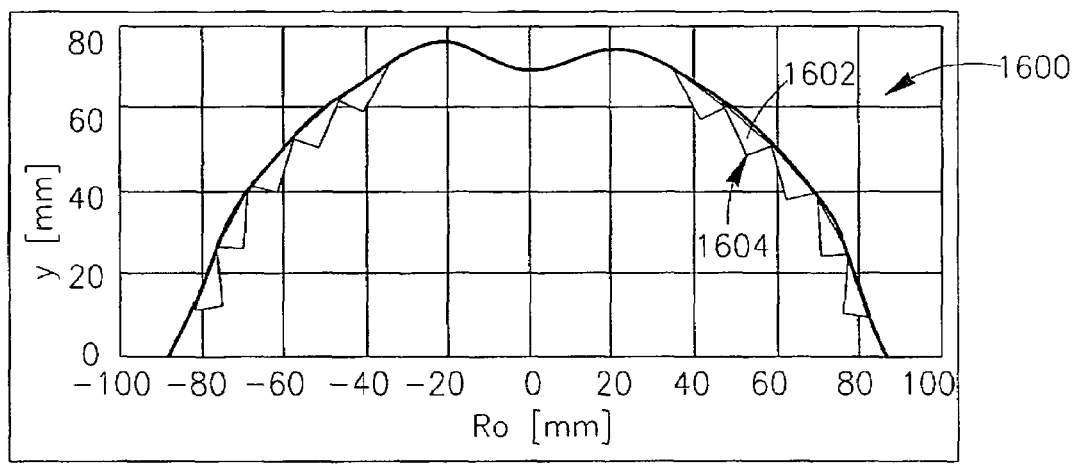
FIG. 16 is a schematic illustration of a grooved reflector according to some demonstrative embodiments of the invention.

Reference is now made to FIG. 16, which schematically illustrates a grooved reflector 1600 according to some demonstrative embodiments of the invention. Although the invention is not limited in this respect, reflector 1600 may perform the functionality of reflector 921 (FIG. 9). Reflector 1600 may include one or more sections 1604 configured based on one or more respective local light distributions of the customized light flux distribution. For example, sections 1604 may include one or more groves 1602 to locally affect the reflection of the light rays towards chamber 906 (FIG. 9).

Figure 17A:
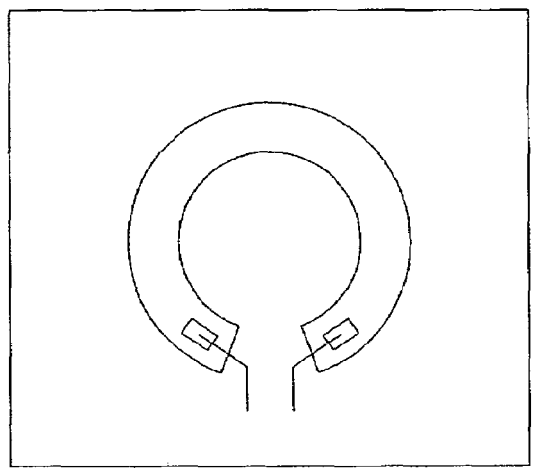
FIG. 17A is a schematic illustration of a donut-shaped lamp according to some demonstrative embodiments of the invention.
Figure 17B:
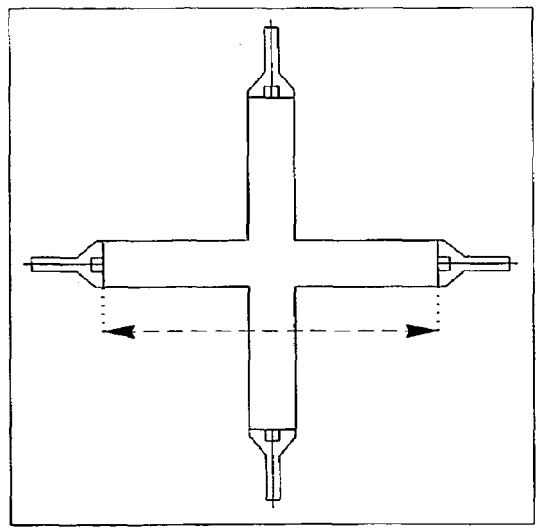
FIG. 17B is a schematic illustration of a cross-shaped lamp according to some demonstrative embodiments of the invention.

Referring back to FIG. 9, according to some demonstrative embodiments of the invention, a shape of lamp 919 may be based at least in part on the customized light flux distribution. In one example, lamp 919 may include a donut-shaped lamp, e.g., as shown in FIG. 17A. In another example, lamp 919 may include a cross-shaped (star) lamp, e.g., as shown in FIG. 17B. In other embodiments, lamp 919 may have any other suitable shape and/or configuration.

According to some demonstrative embodiments of the invention, disinfector 900 may include at least one additional illumination source 999. Although the invention is not limited in this respect, illumination source 999 may include at least one lamp 998, e.g., similar to or different than lamp 919; and/or a reflector 997, e.g., similar to or different than reflector 921. Illumination source 999 may be configured based on the customized light flux distribution. In some demonstrative embodiments, disinfector 900 may also include at least one additional window, e.g., window 993, to transmit light generate from illumination source into chamber 906.

According to some demonstrative embodiments of the invention, illumination source 999 may be positioned substantially opposite to illumination source 902. For example, illumination source 999 may be proximal to outlet 912.

Disinfector 900 may include any other suitable configuration of illumination sources, windows, reflectors and/or lamps, in addition to or instead of illumination sources 902 and/or 999. For example, disinfector 900 may include one or more lamps (not shown) located along an external surface of chamber 906.

Although the invention is not limited in this respect, disinfector 900 may also include an outlet flow adapter 994 configured to adapt the flow of the medium at outlet 912, e.g., based on the intended distribution of flow velocities. Although the invention is not limited in this respect, flow adapter 994 may be cylindrically shaped, wherein an inner diameter of flow adapter 994 may be larger than an inner diameter of outlet 912. It will be appreciated that this configuration may enable adapting the flow at outlet 912 such that at least part of the entities flowing along different tracks, e.g., substantially all the entities, have substantially the same velocity at outlet 912. In one demonstrative embodiment, flow adapter 994 and/or outlet 912 may be configured such that for a cylindrical chamber, the quantity of water flowing outward from a small angular segment around the chamber at a given unit time, may be substantially equal to the quantity of water flowing outward from another small angular segment around the chamber at the given unit time. For example, the outward flow rate may be substantially "cylindrically" symmetric.

Following, are examples relating to illumination flux distributions in accordance with some demonstrative embodiments of the invention. It should be noted that the illumination-flux distributions used in these examples are not intended to limit the scope of the invention to any particular disinfector configuration and/or illumination flux distribution.

Figure 18A:
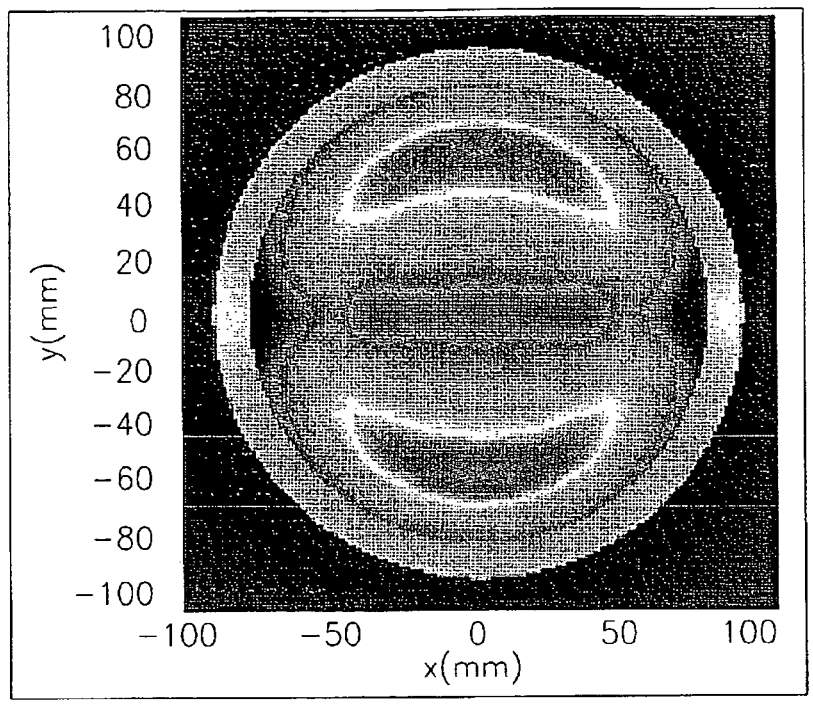
FIGS. 18A, 18B, and 18C are schematic illustrations of three cross sections, respectively, of a first light flux distribution within a chamber according to a first demonstrative embodiment of the invention.
Figure 18B:
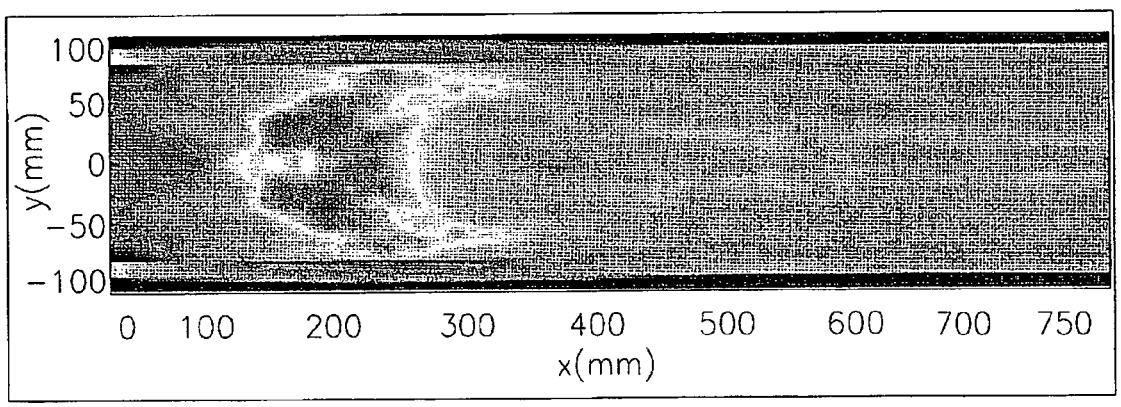
Figure 18C:
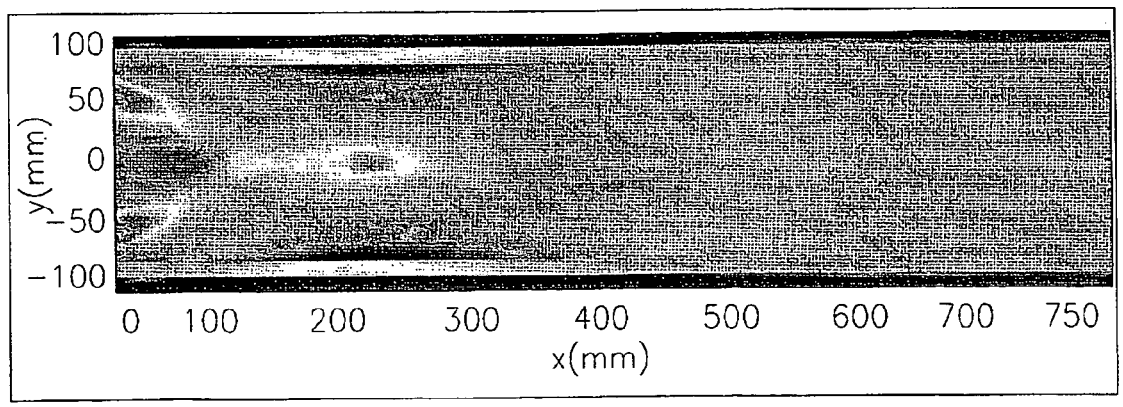

FIGS. 18A, 18B, and 18C illustrate three cross sections, respectively, of a first light flux distribution within chamber 906, according to a first demonstrative embodiment of the invention. The first light flux distribution may be achieved, for example, using a spheroid reflector having a radius R=110 mm.

Figure 19A:
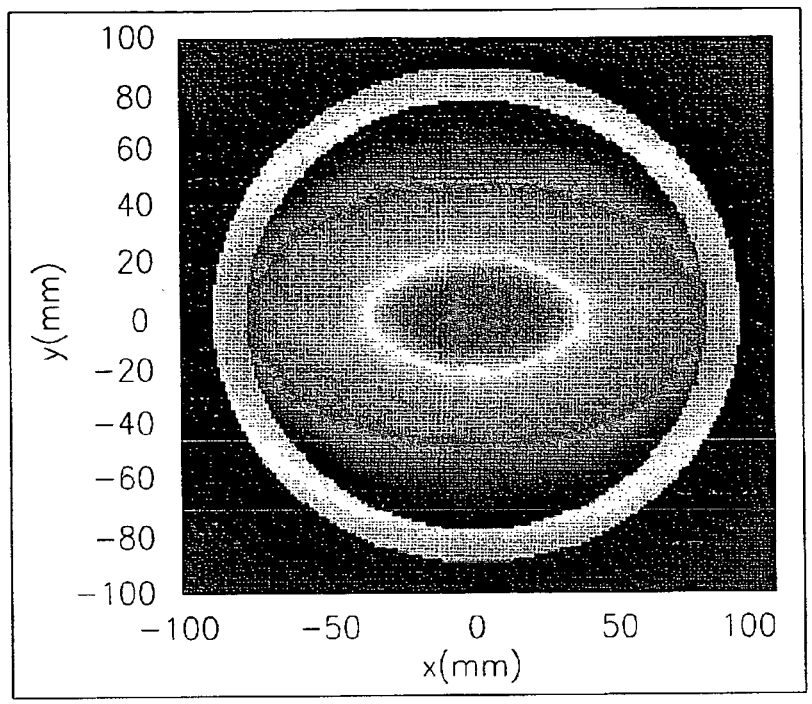
FIGS. 19A, 19B, and 19C are schematic illustrations of three cross sections, respectively, of a second light flux distribution within a chamber according to a second demonstrative embodiment of the invention.
Figure 19B:
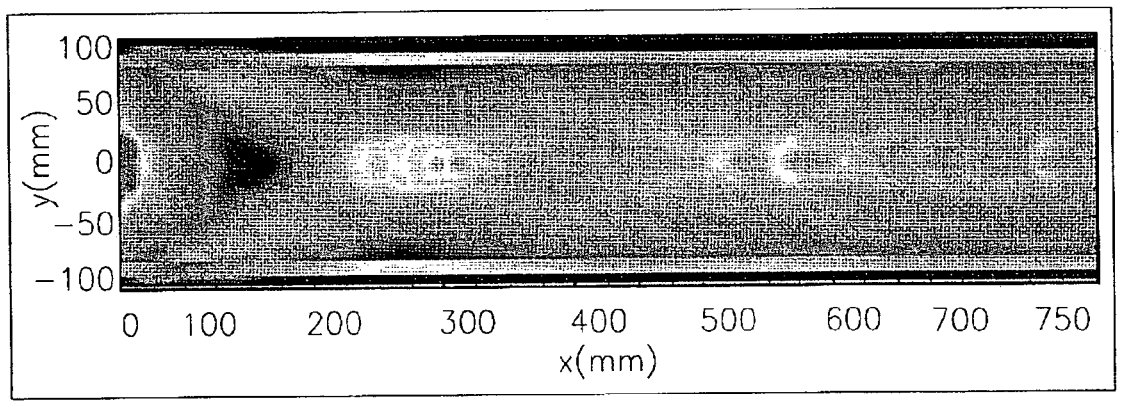
Figure 19C:
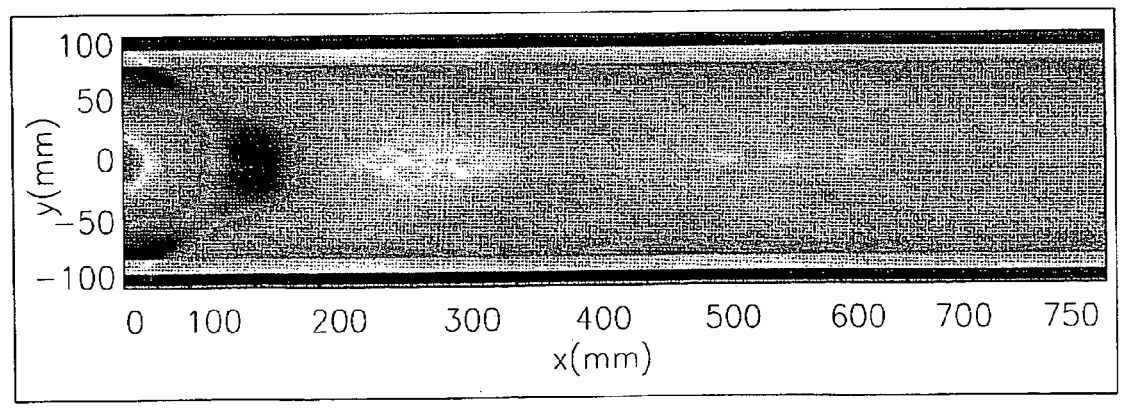

FIGS. 19A, 19B, and 19C illustrate three cross sections, respectively, of a second light flux distribution within chamber 906, according to a second demonstrative embodiment of the invention. The second light flux distribution may be achieved, for example, using an a-spherical reflector having a first set of attributes.

Figure 20A:
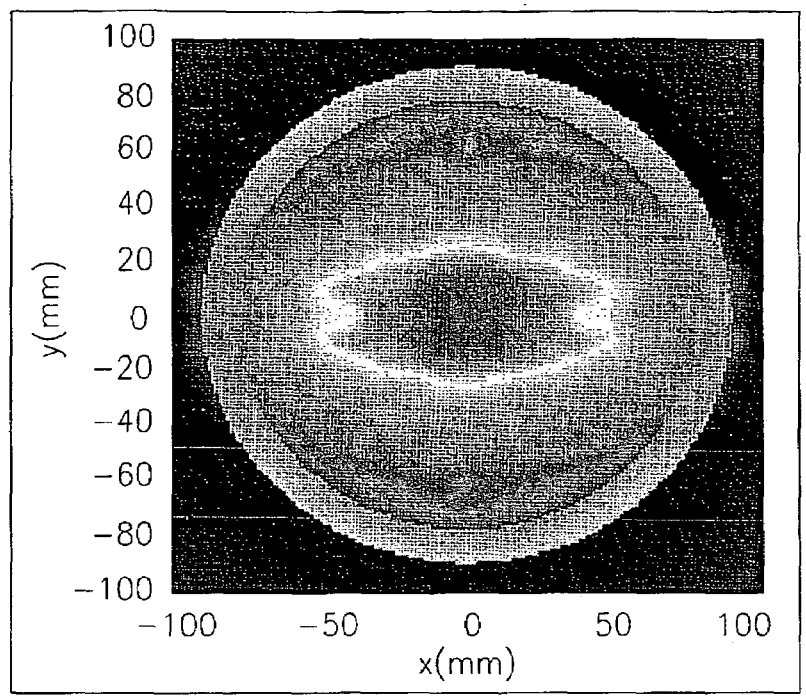
FIGS. 20A, 20B, and 20C are schematic illustrations of three cross sections, respectively, of a third light flux distribution within a chamber according to a third demonstrative embodiment of the invention.
Figure 20B:
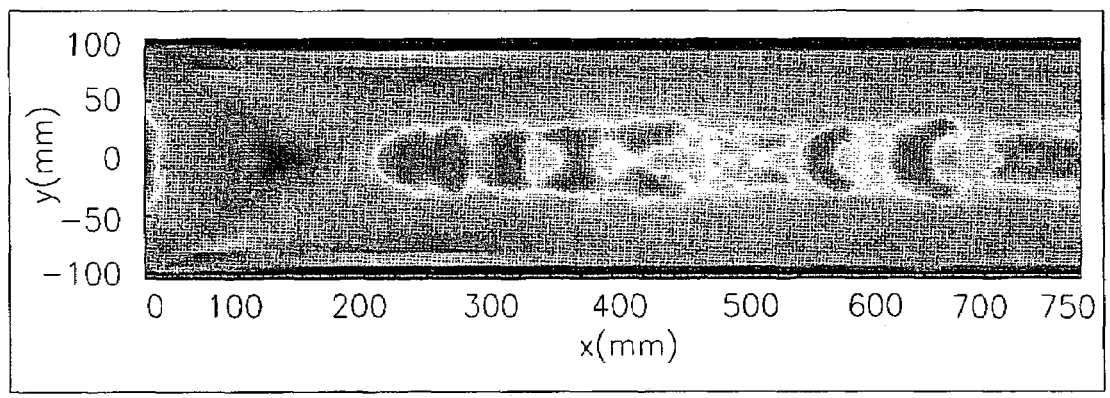
Figure 20C:
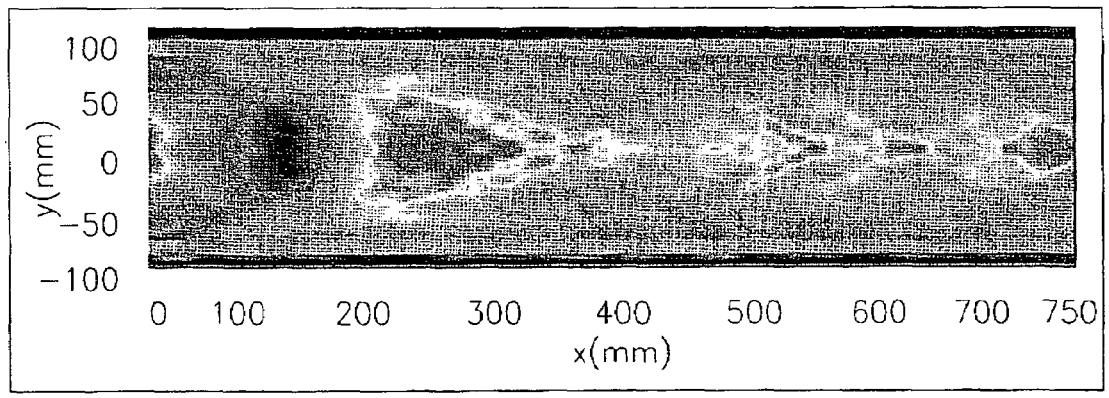

FIGS. 20A, 20B, and 20C illustrate three cross sections, respectively, of a third light flux distribution within chamber 906, according to a third demonstrative embodiment of the invention. The third light flux distribution may be achieved, for example, using an a-spherical reflector having a second set of attributes.

Figure 21A:
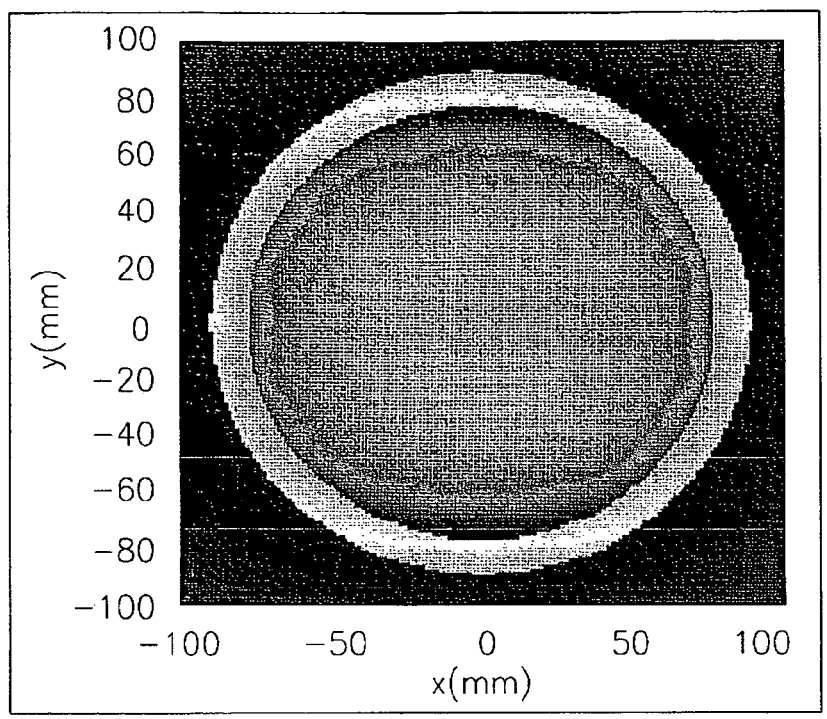
FIGS. 21A, 21B, and 21C are schematic illustrations of three cross sections, respectively, of a fourth light flux distribution within a chamber according to a fourth demonstrative embodiment of the invention.
Figure 21B:
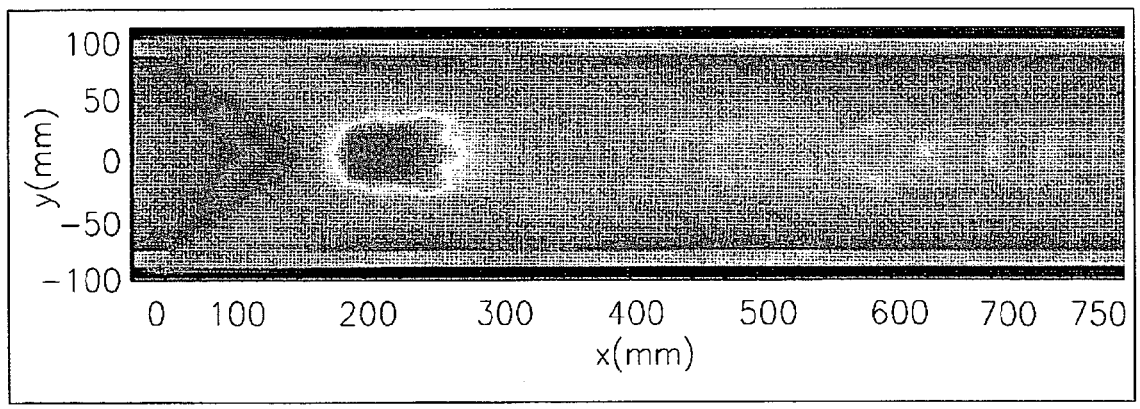
Figure 21C:
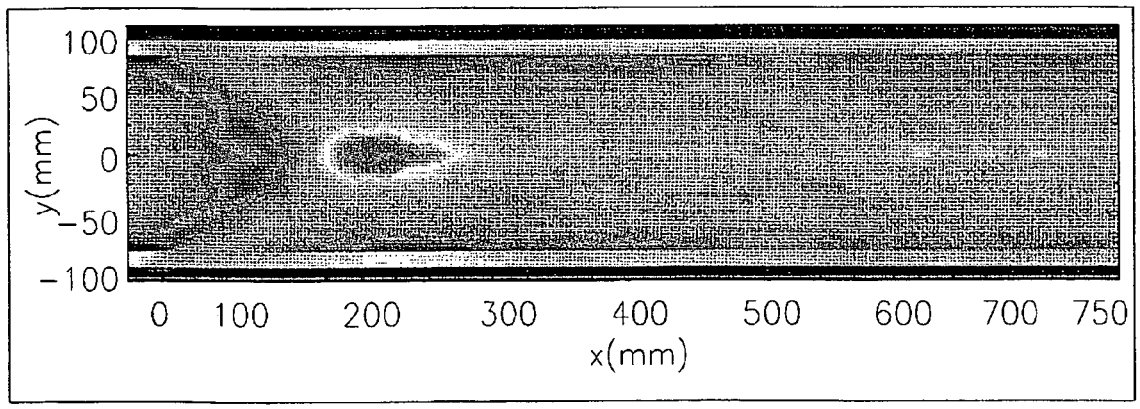

FIGS. 21A, 21B, and 21C illustrate three cross sections, respectively, of a fourth light flux distribution within chamber 906, according to a fourth demonstrative embodiment of the invention. The fourth light flux distribution may be achieved, for example, using an a-spherical reflector having a third set of attributes.

Figure 22A:
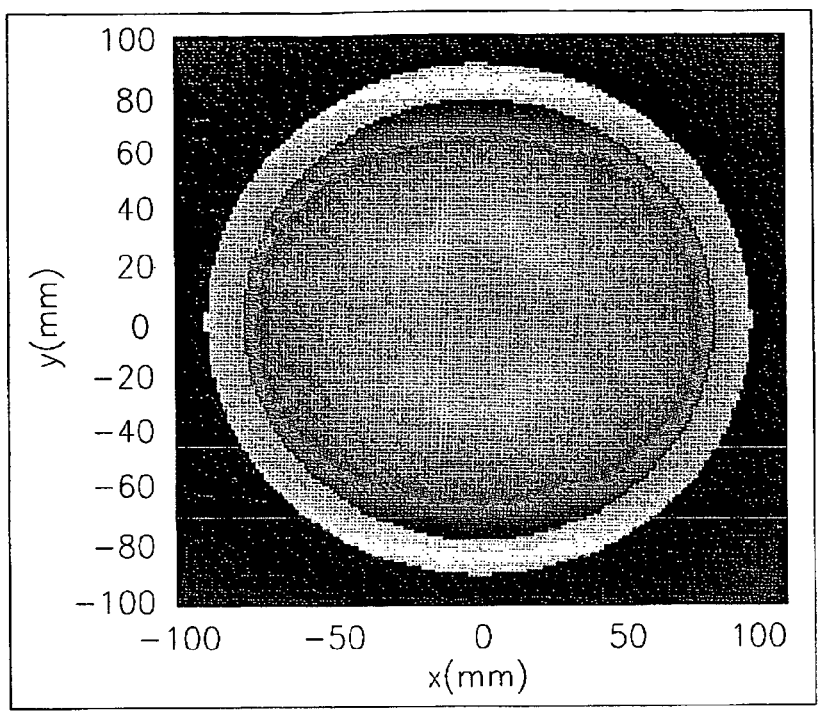
FIGS. 22A, 22B, and 22C are schematic illustrations of three cross sections, respectively, of a fifth light flux distribution within a chamber according to a fifth demonstrative embodiment of the invention.
Figure 22B:
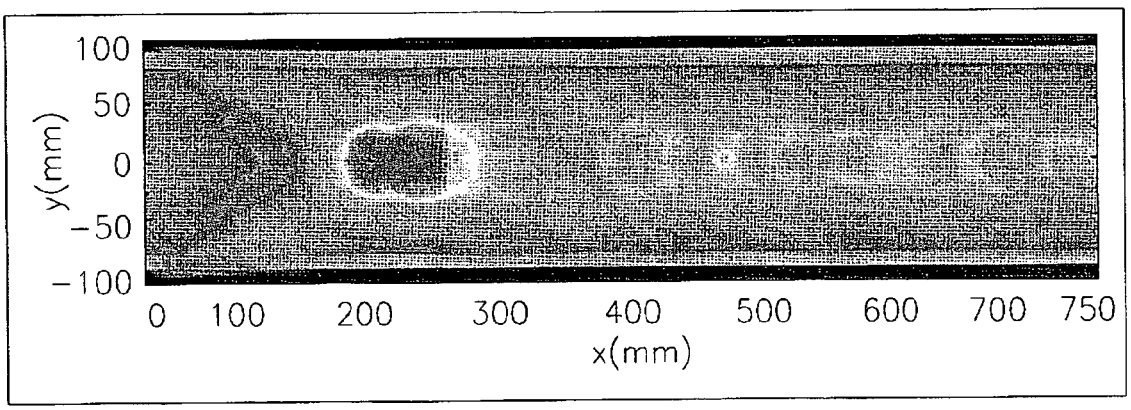
Figure 22C:
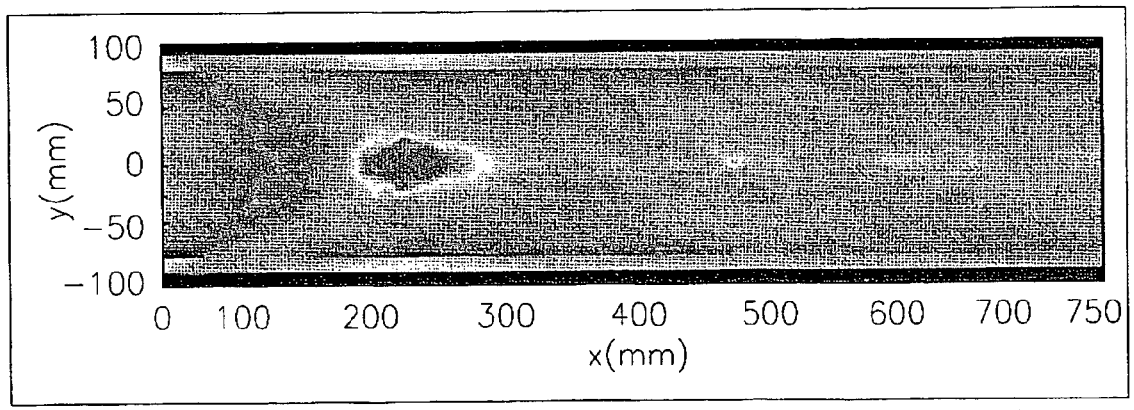

FIGS. 22A, 22B, and 22C illustrate three cross sections, respectively, of a fifth light flux distribution within chamber 906, according to a fifth demonstrative embodiment of the invention. The fifth light flux distribution may be achieved, for example, using an a-spherical reflector having a fourth set of attributes.

As shown in FIGS. 18A-18C, 19A-19C, 20A-20C, 21A-21C, and/or 22A-22C light source 902, reflector 921, lamp 919, and/or window 907 may be configured to generate various light flux distributions within chamber 906. For example, light source 902, reflector 921, lamp 919, and/or window 907 may be configured to generate the customized light flux distribution based on the intended distribution of flow velocities within chamber 906.

Figure 23A:
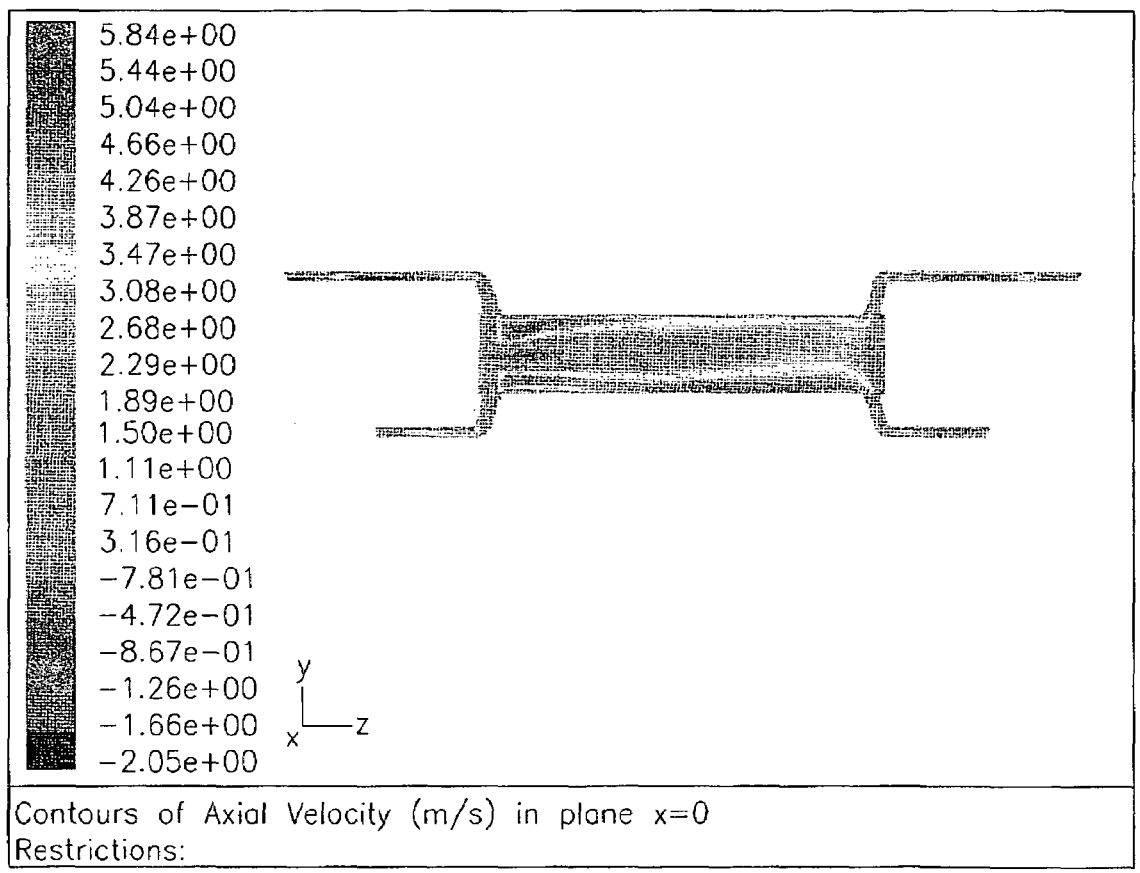
FIGS. 23A and 23B are schematic illustrations of two cross sections, respectively, of an intended distribution of flow velocities within a chamber according to a demonstrative embodiment of the invention.
Figure 23B:
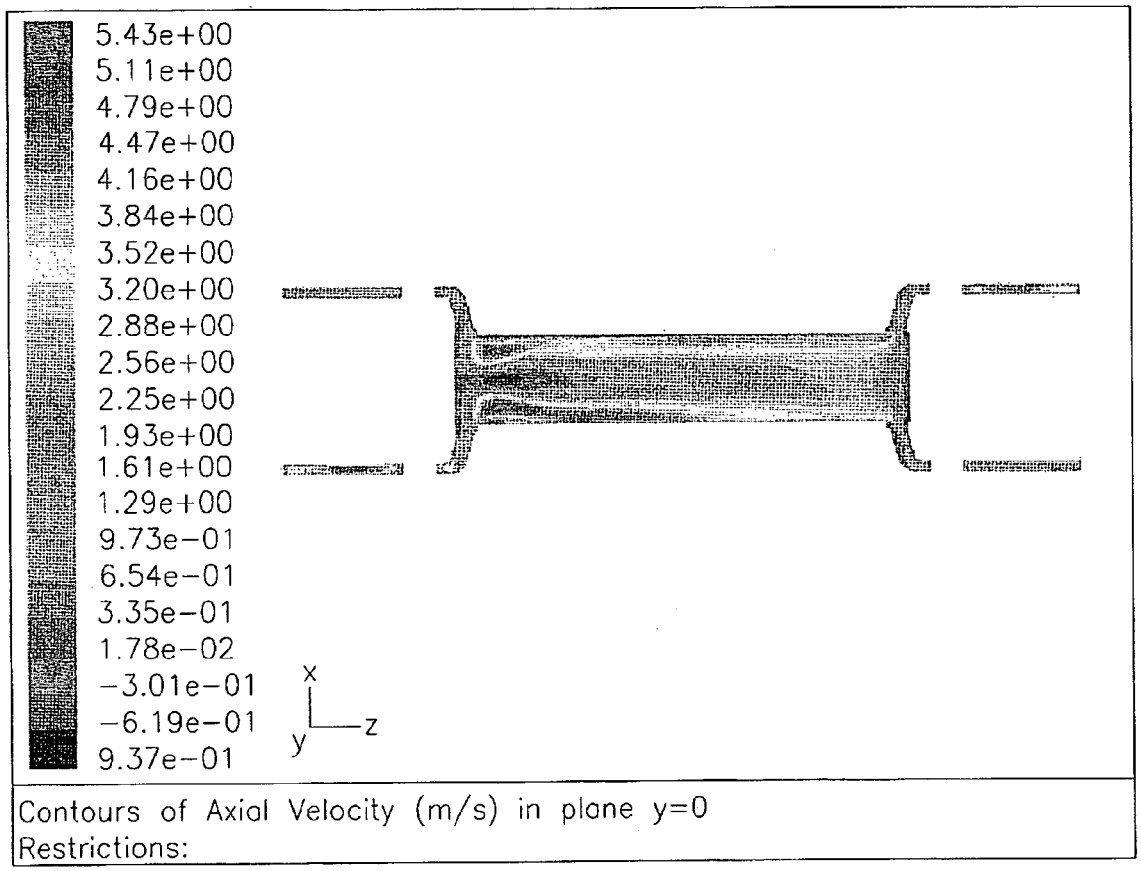

The intended distribution of flow velocities may be determined, evaluated and/or simulated using any suitable method, algorithm, or simulation. For example, the intended distribution of flow velocities may be simulated using flow simulation software, as shown in FIGS. 23A and 23B, which illustrate two cross sections, respectively, of an intended distribution of flow velocities within a disinfector chamber, according to a demonstrative embodiment of the invention.

Embodiments of the present invention may be implemented by software, by hardware, or by any combination of software and/or hardware as may be suitable for specific applications or in accordance with specific design requirements. Embodiments of the present invention may include units and sub-units, which may be separate of each other or combined together, in whole or in part, and may be implemented using specific, multi-purpose or general processors, or devices as are known in the art. Some embodiments of the present invention may include buffers, registers, storage units and/or memory units, for temporary or long-term storage of data and/or in order to facilitate the operation of a specific embodiment.

While certain features of the invention have been illustrated and described herein, many modifications, substitutions, changes, and equivalents may occur to those of ordinary skill in the art. It is, therefore, to be understood that the appended claims are intended to cover all such modifications and changes as fall within the true spirit of the invention.

What is claimed is:

1. An apparatus comprising:
    a conduit to carry a flowing medium to be disinfected, said conduit having an inlet to receive said medium and an outlet to discharge said medium;
    a flow adapter configured to adapt a flow of said medium at said inlet based on an intended spatial distribution of flow velocities of entities suspended in said medium along a plurality of intended flow paths from said inlet to said outlet; and
    at least one illumination source to illuminate said conduit with light having a customized spatial light flux distribution, which is based at least in part on said intended distribution of flow velocities.

2. The apparatus of claim 1, wherein said customized light flux distribution and said intended spatial distribution of flow velocities result in an intended distribution of a plurality of cumulative illumination doses corresponding to said plurality of flow paths, respectively,
    and wherein a ratio of a difference between an average of said cumulative illumination doses and a minimum of said cumulative illumination doses to said average is smaller than 0.7.

3. The apparatus of claim 2, wherein each of said cumulative illumination doses comprises a sum of ratios related to a path of said plurality of paths, wherein said sum of ratios comprises a sum of ratios between intended light intensities resulting from said customized light flux at a plurality of locations along said path and intended flow velocities at said plurality of locations.

4. The apparatus of claim 1, wherein said conduit comprises an elongated chamber.

5. The apparatus of claim 4, wherein said chamber comprises a tubular chamber, and wherein a first intended light intensity resulting from said customized light flux at a first distance from a rotation-axis of said chamber is smaller than a second intended light intensity resulting from said customized light flux at a second distance from said rotation-axis, which is smaller than said first distance.

6. The apparatus of claim 4, wherein a first intended light intensity resulting from said customized light flux at a first distance from an inner surface of said chamber is smaller than a second intended light intensity resulting from said customized light flux at a second distance from said inner surface, which is bigger than said first distance.

7. The apparatus of claim 1, wherein said illumination source is external to said conduit.

8. The apparatus of claim 7, wherein said conduit comprises an illumination window to allow light from said illumination source to enter said conduit.

9. The apparatus of claim 8, wherein one or more optical attributes of said window are based at least in part on said customized light flux distribution.

10. The apparatus of claim 9, wherein said one or more optical attributes comprise a refractive index of said window in a spectrum of said light.

11. The apparatus of claim 8, wherein said at least one illumination source comprises two or more illumination sources.

12. The apparatus of claim 11, wherein said two or more illumination sources comprise a first set of one or more lamps positioned substantially opposite to a second set of one or more lamps.

13. The apparatus of claim 11, wherein said two or more illumination sources comprise a first set of one or more lamps proximal to said inlet, and a second set of one or more lamps proximal to said outlet.

14. The apparatus of claim 1, wherein said illumination source comprises:
at least one lamp configured to generate light of a predefined distribution; and
at least one reflector to reflect at least part of the light generated by said at least one lamp,
wherein the light having said customized light flux distribution comprises a combination of the light generated by said lamp and light reflected by said reflector.

15. The apparatus of claim 14, wherein one or more sections of said reflector are configured based on one or more local light flux distributions of said customized light flux distribution.

16. The apparatus of claim 14, wherein said reflector comprises an elliptic reflector.

17. The apparatus of claim 14, wherein said reflector comprises a spheroid reflector.

18. The apparatus of claim 14, wherein a shape of said lamp is based at least in part on said customized light flux distribution.

19. The apparatus of claim 18, wherein said lamp comprises a donut-shaped lamp.

20. The apparatus of claim 18, wherein said lamp comprises a cross-shaped lamp.

21. The apparatus of claim 14, wherein one or more attributes of said reflector are based at least in part on one or more dimensions of said conduit.

22. The apparatus of claim 21, wherein the one or more dimensions of said conduit comprise an inner diameter of said conduit.

23. The apparatus of claim 1, wherein a configuration of said conduit is based at least in part on said intended distribution of flow velocities.

24. The apparatus of claim 23, wherein a configuration of at least one of said inlet and outlet is based at least in part on said intended distribution of flow velocities.

25. The apparatus of claim 1, wherein said conduit comprises a quartz conduit.

26. The apparatus of claim 1, wherein said light comprises ultraviolet light.

27. The apparatus of claim 1, wherein said medium comprises a liquid.

28. The apparatus of claim 27, wherein said liquid comprises water.

29. The apparatus of claim 1, wherein said entities comprise microorganisms.

30. A method of illumination-based disinfection of a medium flowing between an inlet of a conduit and an outlet of said conduit, said method comprising:
adapting a flow of said medium at said inlet based on an intended spatial distribution of flow velocities of entities suspended in said medium along a plurality of intended flow paths from said inlet to said outlet; and
illuminating said conduit with light having a customized spatial light flux distribution which is based at least in part on said intended distribution of flow velocities.

31. The method of claim 30, wherein said customized light flux distribution results in an intended distribution of a plurality of cumulative illumination doses corresponding to said plurality of flow paths, respectively, and wherein a ratio of a difference between an average of said plurality of cumulative illumination doses and a minimum of said plurality of cumulative illumination doses to said average is smaller than 0.7.

32. The method of claim 31, wherein each of said cumulative illumination doses comprises a sum of ratios related to a path of said plurality of paths, wherein said sum of ratios comprises a sum of ratios between intended light intensities resulting from said customized light flux at a plurality of locations along said path and intended flow velocities at said plurality of locations.

33. The method of claim 30, wherein illuminating said conduit comprises illuminating a tubular chamber, and wherein a first intended light intensity resulting from said customized light flux at a first distance from a rotation-axis of said chamber is smaller than a second intended light intensity resulting from said customized light flux at a second distance from said rotation-axis, which is smaller than said first distance.

34. The method of claim 30, wherein illuminating said conduit comprises illuminating said conduit such that a first intended light intensity resulting from said customized light flux at a first distance from an inner surface of said conduit is smaller than a second intended light intensity resulting from said customized light flux at a second distance from said inner surface, which is bigger than said first distance.

35. The method of claim 30, wherein illuminating said conduit comprises externally illuminating said conduit.

36. The method of claim 35, wherein externally illuminating said conduit comprises passing light through an illumination window of said conduit.

37. The method of claim 30, wherein illuminating said conduit comprises:
generating light of a predefined distribution; and
reflecting at least part of the generated light,
wherein the light having said customized light flux distribution comprises a combination of the generated light and the reflected light.

38. The method of claim 30, wherein said light comprises ultraviolet light.

39. The method of claim 30, wherein said medium comprises a liquid.

40. The method of claim 39, wherein said liquid comprises water.

* * * * *